US012600727B2

(12) United States Patent
Sibley et al.

(10) Patent No.: US 12,600,727 B2
(45) **Date of Patent: *Apr. 14, 2026**

(54) TREATMENT OF INFECTIONS OF TOXOPLASMA GONDII AND CLOSELY RELATED PARASITES

(71) Applicants: WASHINGTON UNIVERSITY, St. Louis, MO (US); THE BROAD INSTITUTE, INC., Cambridge, MA (US); PRESIDENT AND FELLOWS OF HARVARD COLLEGE, Cambridge, MA (US)

(72) Inventors: L. David Sibley, St. Louis, MO (US); Joshua Radke, St. Louis, MO (US); Eamon Comer, Cambridge, MA (US); Marshall Morningstar, Cambridge, MA (US); Bruno Melillo, Cambridge, MA (US)

(73) Assignees: WASHINGTON UNIVERSITY, St. Louis, MO (US); THE BROAD INSTITUTE, INC., Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 707 days.

This patent is subject to a terminal disclaimer.

(21) Appl. No.: 17/276,997

(22) PCT Filed: Sep. 18, 2019

(86) PCT No.: PCT/US2019/051686

§ 371 (c)(1),
(2) Date: Mar. 17, 2021

(87) PCT Pub. No.: WO2020/061167

PCT Pub. Date: Mar. 26, 2020

(65) Prior Publication Data

US 2022/0033404 A1 Feb. 3, 2022

Related U.S. Application Data

(60) Provisional application No. 62/732,911, filed on Sep. 18, 2018.

(51) Int. Cl.
*C07D 487/04* (2006.01)
*A61K 31/505* (2006.01)
(Continued)

(52) U.S. Cl.
CPC .......... *C07D 487/04* (2013.01); *A61K 31/505* (2013.01); *A61K 31/635* (2013.01); *A61K 31/7056* (2013.01); *A61P 33/10* (2018.01)

(58) Field of Classification Search
CPC ...... C07D 487/04; A61P 33/10; A61K 31/505
(Continued)

(56) References Cited

U.S. PATENT DOCUMENTS 10,059,711 B2 * 8/2018 Comer et al. ........ C07D 487/04
10,738,055 B2 8/2020 Comer et al.
(Continued)

FOREIGN PATENT DOCUMENTS

WO 2015/070204 A1 5/2015
WO 2018175385 A1 9/2018

OTHER PUBLICATIONS

Andrews KT, Fisher G, Skinner-Adams TS. Drug repurposing and human parasitic protozoan diseases. International Journal for Parasitology: Drugs and Drug Resistance. Aug. 1, 2014;4(2):95-111. (Year: 2014).*

(Continued)

*Primary Examiner* — Jeffrey S Lundgren
*Assistant Examiner* — Heather Dahlin
(74) *Attorney, Agent, or Firm* — Greenberg Traurig, LLP; Melissa Hunter-Ensor; Scott Goncher

(57) ABSTRACT

Provided herein are compounds useful for the treatment of diseases caused by infections of *T. gondii*, and closely related parasites. These compounds, as well as pharmaceutically acceptable salts thereof may be formulated in pharmaceutical compositions including veterinary compositions and may be used in methods of treatment and/or prophylaxis of disease.

18 Claims, 1 Drawing Sheet

(51) Int. Cl.
*A61K 31/635* (2006.01)
*A61K 31/7056* (2006.01)
*A61P 33/10* (2006.01)

(58) Field of Classification Search
USPC .................................................... 514/210.16
See application file for complete search history.

(56) References Cited

U.S. PATENT DOCUMENTS

| | | | | |
|---|---|---|---|---|
| 11,174,260 | B2 * | 11/2021 | Comer et al. | A61K 31/397 |
| 11,325,913 | B2 | 5/2022 | Comer et al. | |
| 12,414,935 | B2 * | 9/2025 | Sibley et al. | C07D 487/04 |
| 2016/0289235 | A1 | 10/2016 | Comer et al. | |
| 2018/0194768 | A1 | 7/2018 | Maianti et al. | |
| 2020/0095253 | A1 | 3/2020 | Comer et al. | |
| 2022/0162211 | A1 | 5/2022 | Comer et al. | |
| 2022/0193034 | A1 | 6/2022 | Sibley et al. | |

OTHER PUBLICATIONS

U.S. Appl. No. 17/604,732, filed Apr. 23, 2019, Compounds and Methods for the Treatment of Parasit.*

U.S. Appl. No. 18/188,249, filed Sep. 24, 2020, Apicomplexan Parasite Inhibition.*

U.S. Appl. No. 17/387,639, Jul. 2021, Compounds and Methods for the Treatment of.*

Radke JB, Carey KL, Shaw S, Metkar SR, Mulrooney C, Gale JP, Bittker JA, Hilgraf R, Comer E, Schreiber SL, Virgin HW. High throughput screen identifies interferon γ-dependent inhibitors of Toxoplasma gondii growth. ACS infectious diseases. Jul. 30, 2018;4(10):1499-507. (Year: 2018).*

Radke JB, Burrows JN, Goldberg DE, Sibley LD. Evaluation of current and emerging antimalarial medicines for inhibition of Toxoplasma gondii growth in vitro. ACS infectious diseases. Jul. 12, 2018;4(8):1264-74. (Year: 2018).*

Andrews KT, Fisher G, Skinner-Adams TS. Drug repurposing and human parasitic protozoan diseases. International Journal for Parasitology: Drugs and Drug Resistance. Aug. 1, 2014;4(2):95-111. (Year: 2018).*

Kato N, Comer E, Sakata-Kato T, Sharma A, Sharma M, Maetani M, Bastien J, Brancucci NM, Bittker JA, Corey V, Clarke D. Diversity-oriented synthesis yields novel multistage antimalarial inhibitors. Nature. Oct. 20, 2016;538(7625):344-9. (Year: 2016).*

Antczak M, Dzitko K, Długońska H. Human toxoplasmosis—Searching for novel chemotherapeutics. Biomedicine & Pharmacotherapy. Aug. 1, 2016;82:677-84. (Year: 2016).*

Pubchem 54666421 Deposit date Dec. 20, 2011 (Dec. 20, 2011) pp. 1-10. Entire Document, especially p. 8 and p. 9.

International Search Report and Written Opinion in PCT International Application No. PCT/US2019/051686 mailed Dec. 4, 2019.

Hopper et al., "Discovery of Selective Toxoplasma gondii Dihydrofolate Reductase Inhibitors for the Treatment of Toxoplasmosis," Journal of Medicinal Chemistry, 2019, vol. 62, pp. 1562-1576.

Seeber et al., "*Escherichia coli* β-galactosidase as an in vitro and in vivo reporter enzyme and stable transfection marker in the intracellular protozoan parasite Toxoplasma gondii," Gene, 1996, vol. 169, pp. 39-45.

* cited by examiner

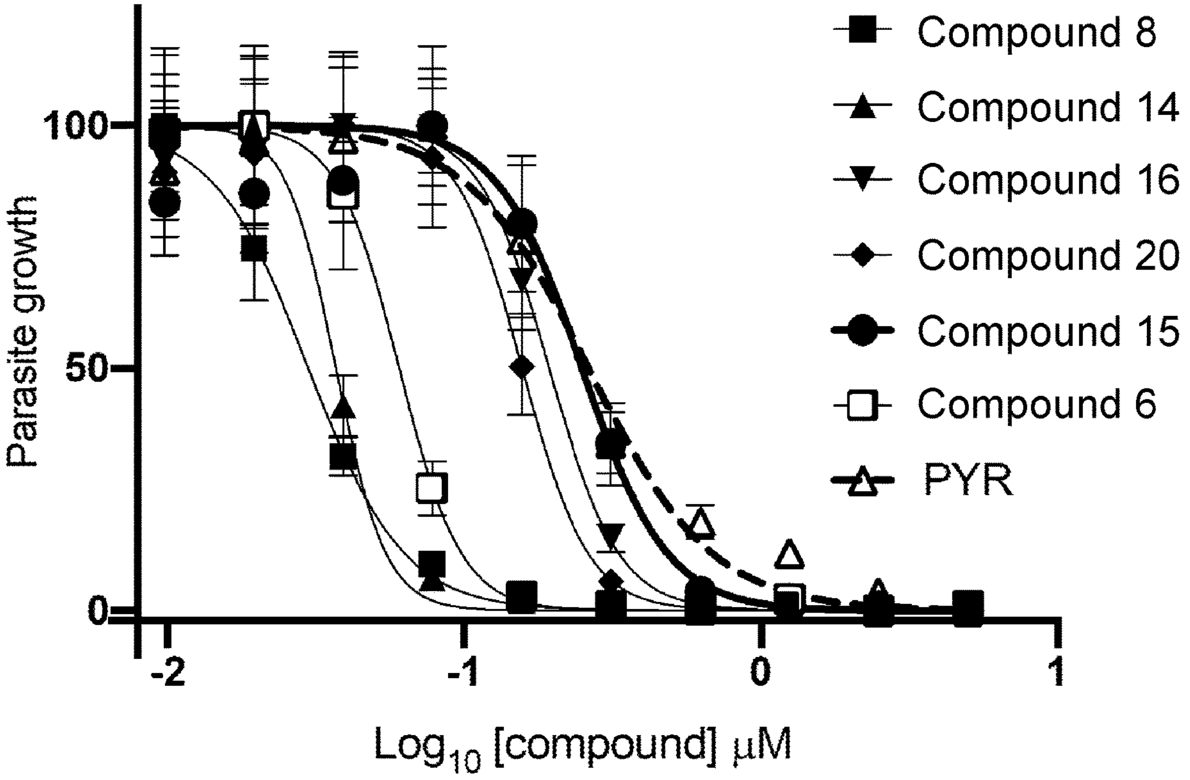
100
50
0
Parasite growth
-2
-1
0
1
Log10 [compound] μM
Compound 8
Compound 14
Compound 16
Compound 20
Compound 15
Compound 6
PYR

TREATMENT OF INFECTIONS OF TOXOPLASMA GONDII AND CLOSELY RELATED PARASITES

CROSS REFERENCE TO RELATED APPLICATIONS

The present application is the U.S. national phase application, pursuant to 35 U.S.C. § 371, of PCT International Application No.: PCT/US2019/051686, filed Sep. 18, 2019, designating the United States and published in English, which claims priority to U.S. App. No. 62/732,911, filed Sep. 18, 2018, each of which is hereby incorporated by reference in its entirety.

STATEMENT OF RIGHTS TO INVENTIONS MADE UNDER FEDERALLY SPONSORED RESEARCH

This invention was made with government support under AI109725 and AI143857 awarded by the National Institutes of Health. The government has certain rights in the invention

PARTIES TO A JOINT RESEARCH AGREEMENT

The claimed invention was made by, on behalf of, and/or in connection with a joint research agreement between The Broad Institute, Inc. and Washington University. The joint research agreement was in effect on and before the effective filing date of the claimed invention, and the claimed invention was made as a result of activities undertaken within the scope of the joint research agreement.

BACKGROUND

*Toxoplasma gondii* is parasite capable of infecting most warm-blooded animals and it causes the disease toxoplasmosis. The only known definitive host of the parasite are cats, which shed oocysts into the environment and these can then readily infect wild and domesticated herbivorous animals. Both wild and domestic cats are susceptible to infection, and although cats normally do not suffer from disease they remain a risk for humans due to their potential to transmit the infection. Upon subject infection, the parasites undergo a brief acute phase during which the parasite propagates as fast growing tachyzoites that disseminate to all organs of the body. Following the acute phase, the parasite differentiates into slow growing bradyzoites residing in long-lived tissue cysts forming in differentiated cells such as neurons and muscle cells. Infections can be passed vertically, resulting in congenital infection, or through oral ingestion of tissue cysts due to omnivorous or carnivorous feeding. Humans often become infected from water or food born contamination or via congenital infection. Although most infections are benign, a large proportion of the world's human population is chronically infected, thereby putting this infected population at risk of reactivation upon a decline in immune surveillance of the host. Additionally, in some regions of South America, toxoplasmosis is associated with severe outcomes including more severe ocular disease even in healthy adults.

The population structure of *T. gondii* is comprised of 6 major clades, each of which contains several related haplotypes. In North America and Europe, animal and human infections are predominantly caused by type 1 (reference strains GT-1, RH (Clade A), type 2 (reference strain ME49 (Clade D) and type 3 (reference strains VEG, CTG (Clade C) strains. The majority of human cases of toxoplasmosis in Europe and North America are due to type 2 strains. Type 1 strains are also reasonably abundant in North America, and they are of interest as they are more pathogenic in many hosts including immunocompromised humans. Type 3 strains are much less pathogenic in animals and also rarely found to infection humans, a trait that may result from their enhanced susceptibility to clearance by macrophages. In contrast to North America and Europe, strains in South America are dominated by highly pathogenic lines such as type 4/8 (reference strains MAS, CtBr5 (CLADE B), type 5 (reference strain RUB (CLADE F), and type 10 (reference strain VAND (CLADE F). The VAND and RUB strains were isolated from severe human cases of toxoplasmosis that are characteristic of the Amazon region. In addition, type 6 (reference strain FOU (Clade A)) is broadly distributed.

Current therapies for treatment of toxoplasmosis rely on inhibition of the folate pathway in the parasite, although macrolide antibiotics have also been used with some success. Although these treatments are designed to block DNA replication and protein synthesis in the parasite, respectively, they are not effective in eliminating the tissue cyst forms that are responsible for chronic infection. The effectiveness of these treatments is often augmented by the strong Th1 immune response in infected subjects, which contributes to control of acute infection. However, these treatment modalities cannot eradicate chronic infections, and suffer from toxicity and allergic reactions. Moreover, such treatments relying on the Th1 immune response have less effect on immunocompromised patients. Serological studies suggest that between 1-2 billion people worldwide are chronically infected with *T. gondii* and harbor tissue cysts in their organs and tissues, and thus are at risk of reactivation should their immune system decline.

Related parasites such as *Sarcocystis neurona*, which causes equine protozoal myeloencephalitis in horses, and *Neospora caninum*, which causes neosporosis in cattle and dogs, have inadequate treatment modalities as well.

It is therefore an object of the disclosure to provide compositions and methods of treatment for infections caused by *T. gondii* and closely related parasites thereto.

SUMMARY

Disclosed herein are compounds, pharmaceutical compositions, and methods of treating or preventing parasitic diseases caused by *Toxoplasma gondii* including toxoplasmosis using one or more compounds as described herein. In some embodiments, the pharmaceutical compositions may be used for the treatment and/or prophylaxis of *T. gondii* infection (e.g., acute infection, chronic infection).

The methods of treatment or prophylaxis of *Toxoplasma gondii* infection or a closely related parasite thereto (e.g., *Sarcocystis neurona, Neospora caninum*, etc.) in a subject in need thereof may comprise administering to said subject a compound having the structure of formula (I).

(I)

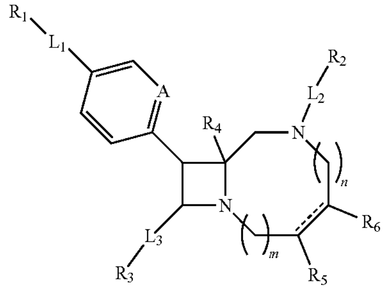

wherein the dashed bond (- - -) may be a single or double bond;

m is 0 (i.e., it is a bond) or 1;

n is 0, 1 or 2;

A is CH or N;

$L_1$ is absent, or —C≡C—;

$L_2$ is absent, alkylene, —C(O)NR—; —$SO_2$—, or —C(O)—;

$L_3$ is absent, alkylene, or heteroalkylene;

$R_1$ is hydrogen, alkyl, heteroalkyl, aryl, heteroaryl, or cycloalkyl, and $R_1$ is optionally substituted;

$R_2$ is perfluoroalkyl, aryl, arylalkyl, alkyl, heteroaryl, or cycloalkyl, and $R_2$ is optionally substituted;

$R_3$ is hydrogen, —OH, —OR, —N(R)S(O)$_2$R, —C(O)R, —NR, or heterocyclyl, and $R_3$ is optionally substituted;

$R_4$ is hydrogen or —$CH_2OH$;

$R_5$ and $R_6$ are independently selected from hydrogen and —OH; and

R is independently selected at each occurrence from hydrogen and lower alkyl, wherein R is optionally substituted.

Compounds are also provided having the structure of formula (I). In certain embodiments, the compounds have the structure of formula (IV):

(IV)

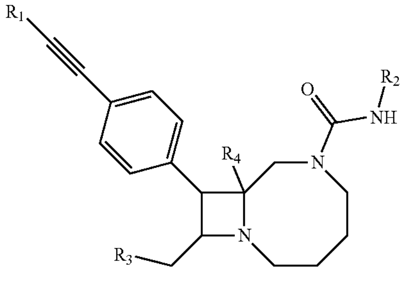

wherein $R_1$ is aryl, heteroaryl, or cycloalkyl, and $R_1$ is optionally substituted with —CN;

$R_2$ is aryl, heteroaryl, or cycloalkyl, and $R_2$ is optionally substituted with halogen or —OR;

$R_3$ is —OR, —N(R)S(O)$_2$R, or heterocyclyl;

$R_4$ is hydrogen or —$CH_2OH$; and

R is independently selected at each occurrence from alkyl or cycloalkyl, and R is optionally substituted with halogen, —OH, or —COOH.

Pharmaceutical compositions are also provided comprising compounds having the structure of formula (I), or pharmaceutically acceptable salts or prodrugs thereof, and one or more pharmaceutically acceptable excipients. In some embodiments, the pharmaceutical composition may be formulated as a veterinary composition.

BRIEF DESCRIPTION OF THE FIGURES

FIG. 1 shows the dose response curves for inhibition of *N. caninum* growth by bicyclic azetidines of the present disclosure. Values represent average of three biological replicates each with two internal replicates and are plotted as mean S.E.M. Pyrimethamine (Pyr) is used as a positive control.

DETAILED DESCRIPTION

Detailed embodiments of the present disclosure are disclosed herein; however, it is to be understood that the disclosed embodiments are merely illustrative of the disclosure that may be embodied in various forms. In addition, each of the examples given in connection with the various embodiments of the disclosure is intended to be illustrative, and not restrictive.

Definitions

It is to be understood that the terminology employed herein is for the purpose of describing particular embodiments, and is not intended to be limiting.

All terms used herein are intended to have their ordinary meaning in the art unless otherwise provided. All concentrations are in terms of percentage by weight of the specified component relative to the entire weight of the topical composition, unless otherwise defined.

As used herein, the articles “a” and “an” refer to one or to more than one (i.e., to at least one) of the grammatical object of the article. By way of example, “an element” means one element or more than one element.

As used herein, all ranges of numeric values include the endpoints and all possible values disclosed between the disclosed values. The exact values of all half integral numeric values are also contemplated as specifically disclosed and as limits for all subsets of the disclosed range. For example, a range of from 0.1% to 3% specifically discloses a percentage of 0.1%, 1%, 1.5%, 2.0%, 2.5%, and 3%. Additionally, a range of 0.1 to 3% includes subsets of the original range including from 0.5% to 2.5%, from 1% to 3%, from 0.1% to 2.5%, etc. It will be understood that the sum of all weight % of individual components will not exceed 100%.

The term “hydrocarbon” refers to a radical or group containing carbon and hydrogen atoms. Examples of hydrocarbon radicals include, without limitation, alkyl, alkenyl, alkynyl, aryl, aryl-alkyl, alkyl-aryl, and any combination thereof (e.g., alkyl-aryl-alkyl, etc.). As used herein, unless otherwise indicated, hydrocarbons may be monovalent or multivalent (e.g., divalent, trivalent, etc.) hydrocarbon radicals. A radical of the form —$(CH_2)_n$—, including a methylene radical, i.e., —$CH_2$—, is regarded as an alkyl radical if it does not have unsaturated bonds between carbon atoms. Unless otherwise specified, all hydrocarbon radicals (including substituted and unsubstituted alkyl, alkenyl, alkynyl, aryl, aryl-alkyl, alkyl-aryl, etc.) will have from 1-20 carbon atoms. In other embodiments, hydrocarbons will have from 1-12 or from 1-8 or from 1-6 or from 1-4 or from 1-3 carbon atoms, including for example, embodiments having one, two, three, four, five, six, seven, eight, nine, or ten carbon atoms.

A "substituted" hydrocarbon may have as a substituent one or more hydrocarbon radicals, substituted hydrocarbon radicals, or may comprise one or more heteroatoms. Examples of substituted hydrocarbon radicals include, without limitation, heterocycles, such as heteroaryls. Unless otherwise specified, a hydrocarbon substituted with one or more heteroatoms will comprise from 1-20 heteroatoms. In other embodiments, a hydrocarbon substituted with one or more heteroatoms will comprise from 1-12 or from 1-8 or from 1-6 or from 1-4 or from 1-3 or from 1-2 heteroatoms. Examples of heteroatoms include, but are not limited to, oxygen, nitrogen, sulfur, phosphorous, halogen (e.g., F, Cl, Br, I, etc.), boron, silicon, etc. In some embodiments, heteroatoms will be selected from the group consisting of oxygen, nitrogen, sulfur, phosphorous, and halogen (e.g., F, Cl, Br, I, etc.). In some embodiments, a heteroatom or group may substitute a carbon. In some embodiments, a heteroatom or group may substitute a hydrogen. In some embodiments, a substituted hydrocarbon may comprise one or more heteroatoms in the backbone or chain of the molecule (e.g., interposed between two carbon atoms, as in "oxa"). In some embodiments, a substituted hydrocarbon may comprise one or more heteroatoms pendant from the backbone or chain of the molecule (e.g., covalently bound to a carbon atom in the chain or backbone, as in "oxo").

In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. It is understood that substitution at a given atom is limited by valency. Common substituents include halo (e.g., F), $C_{1-12}$ straight chain or branched chain alkyl, $C_{2-12}$ alkenyl, $C_{2-12}$ alkynyl, $C_{3-12}$ cycloalkyl, $C_{6-12}$ aryl, $C_{3-12}$ heteroaryl, $C_{3-12}$ heterocyclyl, $C_{1-12}$ alkylsulfonyl, nitro, cyano, —COOR, —C(O)NRR', —OR, —SR, —NRR', and oxo, such as mono- or di- or tri-substitutions with moieties such as halogen, fluoroalkyl, perfluoroalkyl, perfluroalkoxy, trifluoromethoxy, chlorine, bromine, fluorine, methyl, methoxy, pyridyl, furyl, triazyl, piperazinyl, pyrazoyl, imidazoyl, and the like, each optionally containing one or more heteroatoms such as halo, N, O, S, and P. R and R' are independently hydrogen, $C_{1-12}$ alkyl, $C_{1-12}$ haloalkyl, $C_{2-12}$ alkenyl, $C_{2-12}$ alkynyl, $C_{3-12}$ cycloalkyl, $C_{4-24}$ cycloalkylalkyl, $C_{6-12}$ aryl, $C_{7-24}$ aralkyl, $C_{3-12}$ heterocyclyl, $C_{3-24}$ heterocyclylalkyl, $C_{3-12}$ heteroaryl, or $C_{4-24}$ heteroarylalkyl. Unless otherwise noted, all groups described herein optionally contain one or more common substituents, to the extent permitted by valency. Further, as used herein, the phrase "optionally substituted" means unsubstituted (e.g., substituted with H) or substituted. As used herein, the term "substituted" means that a hydrogen atom is removed and replaced by a substituent (e.g., a common substituent). It is understood by one of ordinary skill in the chemistry art that substitution at a given atom is limited by valency. The use of a substituent (radical) prefix names such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon.

As used herein, the term "alkyl," alone or in combination with other groups, refers to a branched or straight-chain monovalent saturated aliphatic hydrocarbon radical of one to twenty carbon atoms (e.g., one to sixteen carbon atoms, one to twelve carbon atoms, one to ten carbon atoms, or one to six carbon atoms, etc.). In some embodiments, the alkyl group may be substituted with 1, 2, 3, or 4 substituent groups as defined herein.

The term "alkylene" as used herein, represents a saturated divalent hydrocarbon group derived from a straight or branched chain saturated hydrocarbon by the removal of two hydrogen atoms, and is exemplified by methylene, ethylene, and isopropylene. In some embodiments, the alkylene may be substituted with 1, 2, 3, or 4 substituent groups as defined herein.

The term "aryl" refers to an aromatic mono- or polycyclic radical of 6 to 12 carbon atoms having at least one aromatic ring. Examples of such groups include, but are not limited to, phenyl, naphthyl, 1,2,3,4-tetrahydronaphthalyl, 1,2-dihydronaphthalyl, indanyl, and 1H-indenyl. In some embodiments, the aryl may be substituted with 1, 2, 3, or 4 substituent groups as defined herein.

The "arylalkyl" group, which as used herein, represents an aryl group, as defined herein, attached to the parent molecular group through an alkylene group, as defined herein. Exemplary unsubstituted arylalkyl groups are from 7 to 30 carbons (e.g., from 7 to 16 or from 7 to 20 carbons, such as $C_{6-10}$ aryl $C_{1-6}$ alkyl, $C_{6-10}$ aryl $C_{1-10}$ alkyl, or $C_{6-10}$ aryl $C_{1-20}$ alkyl). In some embodiments, the arylalkyl may be substituted with 1, 2, 3, or 4 substituent groups as defined herein.

The terms "carbocyclic" and "carbocyclyl," as used herein, refer to an optionally substituted non-aromatic $C_{3-12}$ monocyclic, bicyclic, or tricyclic structure in which the rings are formed by carbon atoms. Carbocyclic structures include cycloalkyl, cycloalkenyl, and cycloalkynyl groups. In some embodiments, the carbocycle may be substituted with 1, 2, 3, or 4 substituent groups as defined herein.

The term "cycloalkyl" refers a monovalent mono- or polycarbocyclic radical of three to ten (e.g. three to six) carbon atoms. This term is further exemplified by radicals such as cyclopropyl, cyclobutyl, cyclopentyl, cyclohexyl, cycloheptyl, norbornyl, adamantyl, and indanyl. In certain embodiments, the "cycloalkyl" moieties can optionally be substituted with one, two, three or four substituents. Each substituent can independently be, alkyl, alkoxy, halogen, amino, hydroxyl or oxygen unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, and optionally substituted cycloheptyl, or those which are specifically exemplified herein. In some embodiments, the cycloalkyl may be substituted with 1, 2, 3, or 4 substituent groups as defined herein.

In some embodiments, hydrocarbons containing one or more heteroatoms (e.g., heteroalkyl, heteroaryl, heterocycle, alkoxy, etc.) may be substituted with 1, 2, 3, or 4 substituent groups as defined herein. Examples of heteroaryl groups are pyridyl, benzooxazolyl, benzoimidazolyl, and benzothiazolyl. Examples of hetereocyclyl groups include, but are not limited to, oxetanyl, morpholinyl, thiomorpholinyl, piperazinyl, piperidinyl, pyrrolidinyl, tetrahydropyranyl, tetrahydrofuranyl, and 1,3-dioxanyl. The heterocyclyl groups may be unsubstituted or substituted, and attachment may be through their carbon frame or through their heteroatom(s) where appropriate.

Compounds provided herein can have one or more asymmetric carbon atoms and can exist in the form of optically pure enantiomers, mixtures of enantiomers such as racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as chiral chromatography and separation methods based thereon. The appropriate technique and/or method for separating an enantiomer of a compound described herein from a racemic mixture can be readily determined by those of skill in the art. "Racemate" or "racemic mixture" means a mixture containing two enantiomers, wherein such mixtures exhibit no optical activity; i.e., they do not rotate the plane of polarized light. "Geometric isomer" means isomers that differ in the orientation of substituent atoms (e.g., to a carbon-carbon double bond, to a cycloalkyl ring, to a bridged bicyclic system, etc.). Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds disclosed herein may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99%, or 99.9%) by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The disclosure embraces all of these forms.

The term "effective amount" or "therapeutically effective amount" of an agent, as used herein, is that amount sufficient to effect beneficial or desired results, such as clinical results, and, as such, an "effective amount" depends upon the context in which it is being applied. For example, in the context of administering an agent that is an antibiotic agent, an effective amount of an agent is, for example, an amount sufficient to achieve alleviation or amelioration or prevention or prophylaxis of one or more symptoms or conditions; diminishment of extent of disease, disorder, or condition; stabilized (i.e., not worsening) state of disease, disorder, or condition; preventing spread of disease, disorder, or condition (e.g., preventing the spread of *T. gondii* infection; delay or slowing the progress of the disease, disorder, or condition; amelioration or palliation of the disease, disorder, or condition; and remission (whether partial or total), whether detectable or undetectable, as compared to the response obtained without administration of the agent.

The term "pharmaceutical composition," as used herein, represents a composition containing a compound described herein formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gel cap, or syrup); for topical administration (e.g., as a cream, gel, lotion, or ointment); for intravenous administration (e.g., as a sterile solution free of particulate emboli and in a solvent system suitable for intravenous use); or in any other formulation described herein (see below).

Useful pharmaceutical carriers for the preparation of the compositions hereof, can be solids, liquids, or gases. Thus, the compositions can take the form of tablets, pills, capsules, suppositories, powders, enterically coated or other protected formulations (e.g., binding on ion-exchange resins or packaging in lipid-protein vesicles), sustained release formulations, solutions, suspensions, elixirs, and aerosols. The carrier can be selected from the various oils including those of petroleum, animal, vegetable or synthetic origin, e.g., peanut oil, soybean oil, mineral oil, and sesame oil. Water, saline, aqueous dextrose, and glycols are examples of liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, gelatin, malt, rice, flour, chalk, silica, magnesium stearate, sodium stearate, glycerol monostearate, sodium chloride, dried skim milk, glycerol, propylene glycol, water, and ethanol. The compositions may be subjected to conventional pharmaceutical additives such as preservatives, stabilizing agents, wetting or emulsifying agents, salts for adjusting osmotic pressure, and buffers. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for administration to the recipient.

As used herein, the term "pharmaceutically acceptable salt" refers to salts of any of the compounds described herein that within the scope of sound medical judgment, are suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, dichloroacetate, digluconate, dodecylsulfate, ethanesulfonate, formate, fumarate, glucoheptonate, glutamate, glycerophosphate, hemisulfate, heptonate, hexanoate, hippurate, hydrobromide, hydrochloride, hydroiodide, 2-hydroxy-ethanesulfonate, isethionate, lactobionate, lactate, laurate, lauryl sulfate, malate, maleate, malonate, mandelate, methanesulfonate, mucate, 2-naphthalenesulfonate, nicotinate, nitrate, oleate, oxalate, palmitate, pamoate, pantothenate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative basic salts include alkali or alkaline earth metal salts include sodium, lithium, potassium, calcium, and magnesium, aluminum salts, as well as nontoxic ammonium, quaternary ammonium, and amine cations, including, but not limited to ammonium, tetramethylammonium, tetraethylammonium, methylamine, dimethylamine, trimethylamine, triethylamine, caffeine, and ethylamine.

As used herein, the term "subject" refers to any organism to which a composition in accordance with the disclosure may be administered, e.g., for experimental, diagnostic, prophylactic, and/or therapeutic purposes. Typical subjects include any animal (e.g., mammals such as mice, rats, rabbits, dogs, non-human primates, and humans, lizards, geckos, etc.). The subject may be domesticated animals (e.g., cows, calves, sheep, goat, lambs, horses, poultry, foals, pigs, piglets, etc.), or animals in the family Muridae (e.g., rats, mice, etc.), or animals in the family Felidae. A subject may seek or be in need of treatment, require treatment, be receiving treatment, may be receiving treatment in the future, or a human or animal that is under care by a trained professional for a particular disease or condition. In some embodiments, the subject may be a domesticated animal.

As used herein, and as well understood in the art, "to treat" a condition or "treatment" of the condition (e.g., the conditions described herein such as toxoplasmosis) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition (e.g., preventing the spread of *T. gondii* infection); delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "unit dosage form" refers to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, gel cap, and syrup (also see below).

Compounds

The present disclosure provides for compounds and pharmaceutical compositions useful for the treatment or prophylaxis of toxoplasmosis caused by *Toxoplasma gondii* or parasites closely related thereto. The disclosure also provides methods of using these compounds and compositions.

The compounds may have the structure of formula (I):

(I)

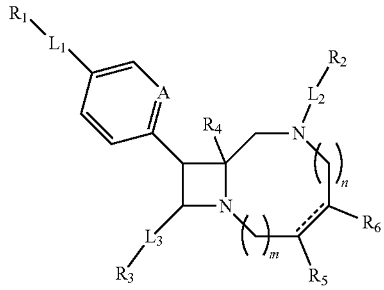

wherein the dashed bond (- - -) may be a single or double bond;

m is 0 (i.e., it is a bond) or 1;

n is 0, 1 or 2;

A is CH or N;

$L_1$ is absent (i.e., it is a bond), or —C≡C—;

$L_2$ is absent, alkylene (e.g., $C_1$-$C_6$ alkylene, etc.), —C(O)NR—; —$SO_2$—, or —C(O)—;

$L_3$ is absent, alkylene (e.g., $C_1$-$C_6$ alkylene, etc.), or heteroalkylene (e.g., $C_1$-$C_6$ heteroalkylene, etc.);

$R_1$ is hydrogen, alkyl (e.g., $C_1$-$C_6$ alkyl, etc.), heteroalkyl (e.g., $C_1$-$C_6$ heteroalkyl, etc.), aryl (e.g., $C_5$-$C_{10}$ aryl, etc.), heteroaryl (e.g., $C_3$-$C_{10}$ heteroaryl, etc.), or carbocyclyl (e.g., $C_3$-$C_{10}$ cycloalkyl, $C_3$-$C_{10}$ cycloalkyl, etc.), and $R_1$ is optionally substituted;

$R_2$ is perfluoroalkyl (e.g., $C_1$-$C_6$ perfluoroalkyl, etc.), aryl (e.g., $C_5$-$C_{10}$ aryl, etc.), arylalkyl (e.g., $C_5$-$C_{10}$ arylalkyl, etc.), alkyl (e.g., $C_1$-$C_6$ alkyl, etc.), heteroaryl (e.g., $C_3$-$C_{10}$ heteroaryl, etc.), or carbocyclyl (e.g., $C_3$-$C_{10}$ carbocycyl, $C_3$-$C_{10}$ cycloalkyl, etc.), and $R_2$ is optionally substituted;

$R_3$ is hydrogen, —OH, —OR, —N(R)S(O)$_2$R, —C(O)R, —NR, or heterocyclyl (e.g., $C_3$-$C_9$ heterocyclyl, $C_3$-$C_9$ heterocycloalkyl, etc.), and $R_3$ is optionally substituted;

$R_4$ is hydrogen or —$CH_2$OH;

$R_5$ and $R_6$ are independently selected from hydrogen and OH; and

R is independently hydrogen or a hydrocarbon (e.g., $C_1$-$C_{10}$ alkyl, $C_3$-$C_{10}$ cycloalkyl, lower alkyl such as methyl, ethyl, propyl, butyl, cyclobutyl, cyclopropyl, etc.), and R is optionally substituted.

The compound may have the structure of formula (II):

(II)

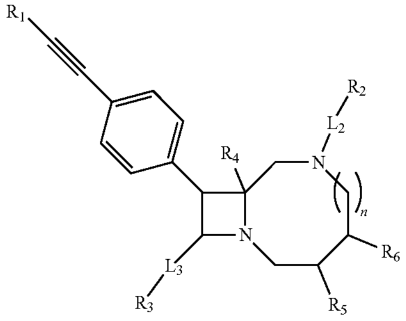

wherein n is 0 (i.e. it is a bond) or 1;

$L_2$ is absent or —C(O)NH—;

$L_3$ is absent or —$CH_2$—

$R_1$ is aryl (e.g., $C_5$-$C_{10}$ aryl, etc.), heteroaryl (e.g., $C_3$-$C_{10}$ heteroaryl, etc.), or cycloalkyl (e.g., $C_3$-$C_{10}$ cycloalkyl, etc.), and $R_1$ is optionally substituted with —CN;

$R_2$ is aryl (e.g., $C_5$-$C_{10}$ aryl, etc.), heteroaryl (e.g., $C_3$-$C_{10}$ heteroaryl, etc.), or cycloalkyl (e.g., $C_3$-$C_{10}$ cycloalkyl, etc.), and $R_2$ is optionally substituted with halogen or —OR;

$R_3$ is hydrogen, —OH, —OR, —N(R)S(O)$_2$R, —NR, or heterocyclyl (e.g., $C_3$-$C_9$ heterocyclyl, $C_3$-$C_9$ heterocycloalkyl, etc.), and $R_3$ is optionally substituted with —R;

$R_4$ is hydrogen or —$CH_2$OH;

$R_5$ and $R_6$ are independently selected from hydrogen and OH; and

R is independently hydrogen or a hydrocarbon (e.g., $C_1$-$C_{10}$ alkyl, $C_3$-$C_{10}$ cycloalkyl, lower alkyl such as methyl, ethyl, propyl, butyl, cyclobutyl, cyclopropyl, etc.) and R is optionally substituted with halogen, —OH, or —COOH. In some embodiments, the compound may have the structure of formula (IIa), (IIb), (IIc) (III), (IV), (IVa), or (IVb):

(IIa)

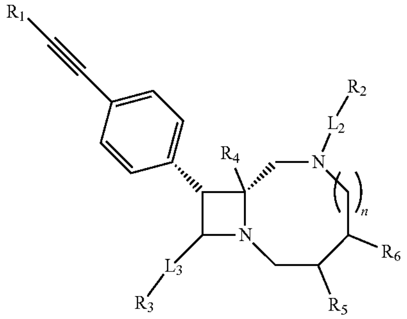

(IIb)

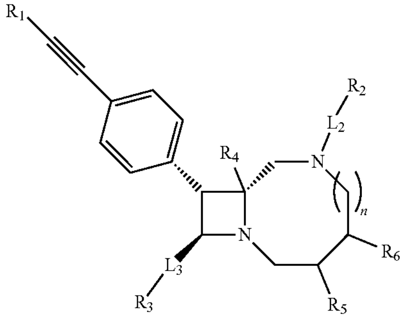

-continued (IIc)

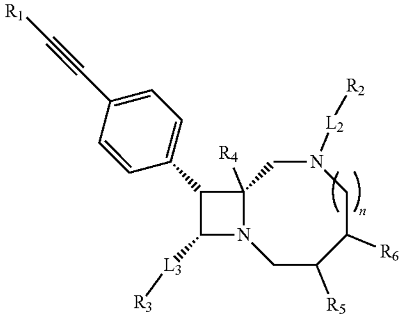

(III)

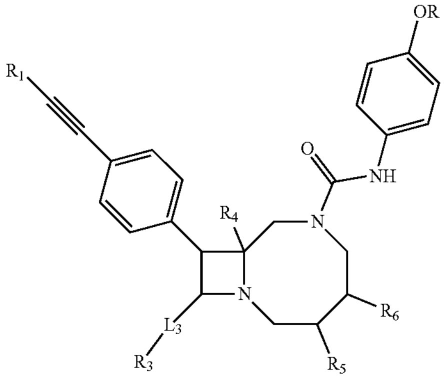

In certain embodiments, $L_2$ may be —C(O)NH— and $R_2$ may be phenyl optionally substituted (e.g., with halogen or —OR). In some embodiments, $R_1$ may be phenyl or pyridinyl. $R_1$ may be optionally substituted with cyano. In some embodiments, $R_5$ and $R_6$ are each hydrogen. In some embodiments, $L_3$ is absent. In some embodiments, $R_3$ is —N(R)$SO_2$R.

For example, the compound may have the structure of formula (IV):

(IV)

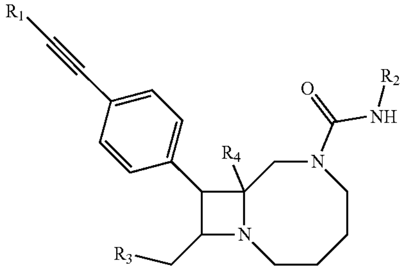

wherein $R_1$ is aryl (e.g., $C_5$-$C_{10}$ aryl, etc.), heteroaryl (e.g., $C_3$-$C_{10}$ heteroaryl, etc.), or cycloalkyl (e.g., $C_3$-$C_{10}$ cycloalkyl, etc.), and $R_1$ is optionally substituted with —CN;

$R_2$ is aryl, heteroaryl (e.g., $C_3$-$C_{10}$ heteroaryl, etc.), or cycloalkyl (e.g., $C_3$-$C_{10}$ cycloalkyl, etc.), and $R_2$ is optionally substituted with halogen or —OR;

$R_3$ is —OR, —N(R)S(O)$_2$R, or heterocyclyl (e.g., $C_3$-$C_9$ heterocyclyl, $C_3$-$C_9$ heterocycloalkyl, etc.);

$R_4$ is hydrogen or —$CH_2$OH; and

R is independently selected at each occurrence from alkyl or cycloalkyl, and R is optionally substituted with halogen, —OH, or —COOH. In some embodiments, the compound has the structure of formula (IVa), (IVb), or (IVc):

(IVa)

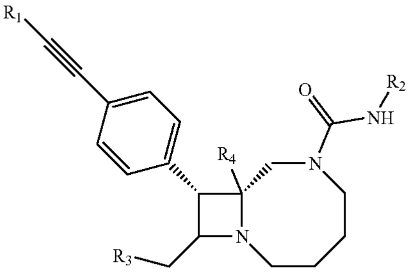

(IVb)

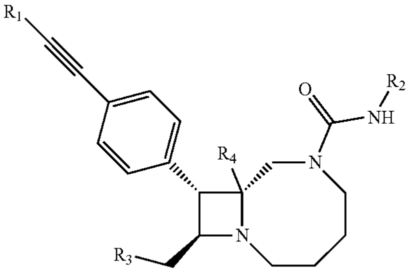

(IVc)

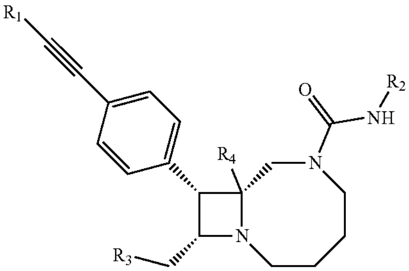

In some embodiments, the compound may be any compound listed in Table 1.

TABLE 1

| Comp. | Structure | Name |
|---|---|---|
| 1 | 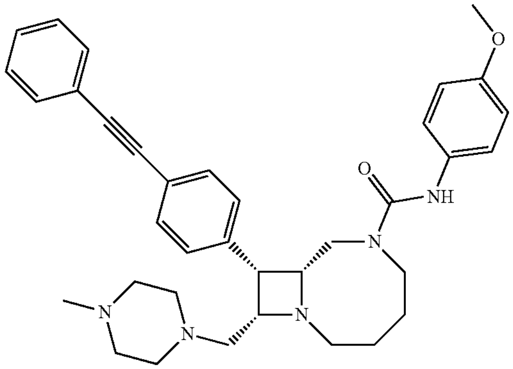 [SMILES: COc1ccc(NC(=O)N2CCCCN3[C@H](CN4CCN(C)CC4)[C@H](c4ccc(C#Cc5ccccc5)cc4)[C@@H]3C2)cc1] | (8R,9S,10S)-N-(4-methoxyphenyl)-10-((4-methylpiperazin-1-yl)methyl)-9-(4-(phenylethynyl)phenyl)-1,6-diazabicyclo[6.2.0]decane-6-carboxamide |
| 2 | 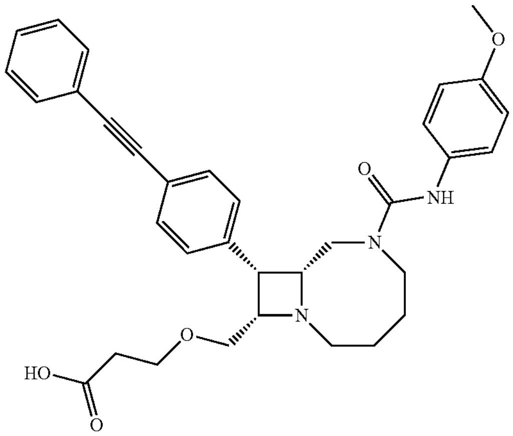 [SMILES: COc1ccc(NC(=O)N2CCCCN3[C@H](COCCC(=O)O)[C@H](c4ccc(C#Cc5ccccc5)cc4)[C@@H]3C2)cc1] | 3-(((8R,9R,10S)-6-((4-methoxyphenyl)carbamoyl)-9-(4-(phenylethynyl)phenyl)-1,6-diazabicyclo[6.2.0]decan-10-yl)methoxy)propanoic acid |
| 3 | 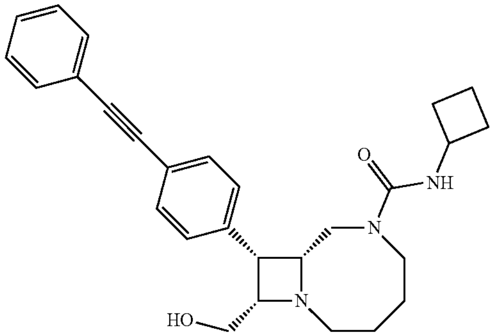 [SMILES: O=C(NC1CCC1)N1CCCCN2[C@H](CO)[C@H](c3ccc(C#Cc4ccccc4)cc3)[C@@H]2C1] | (8R,9R,10S)-N-cyclobutyl-10-(hydroxymethyl)-9-(4-(phenylethynyl)phenyl)-1,6-diazabicyclo[6.2.0]decane-6-carboxamide |
| 4 | 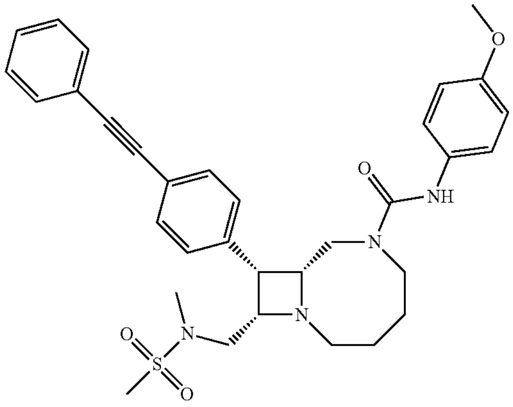 [SMILES: COc1ccc(NC(=O)N2CCCCN3[C@H](CN(C)S(C)(=O)=O)[C@H](c4ccc(C#Cc5ccccc5)cc4)[C@@H]3C2)cc1] | (8R,9R,10S)-N-(4-methoxyphenyl)-10-((N-methylmethylsulfonamido)methyl)-9-(4-(phenylethynyl)phenyl)-1,6-diazabicyclo[6.2.0]decane-6-carboxamide |

TABLE 1-continued

| Comp. | Structure | Name |
| --- | --- | --- |
| 5 | 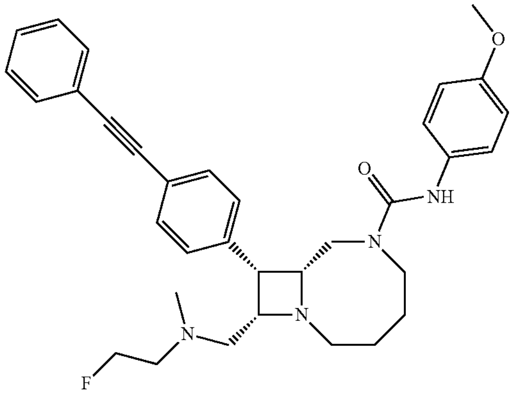 [SMILES: COc1ccc(NC(=O)N2CCCCN3[C@H](CN(C)CCF)[C@H](c4ccc(C#Cc5ccccc5)cc4)[C@@H]3C2)cc1] | (8R,9S,10S)-10-(((2-fluoroethyl)(methyl)amino)methyl)-N-(4-methoxyphenyl)-9-(4-(phenylethynyl)phenyl)-1,6-diazabicyclo[6.2.0]decane-6-carboxamide |
| 6 | 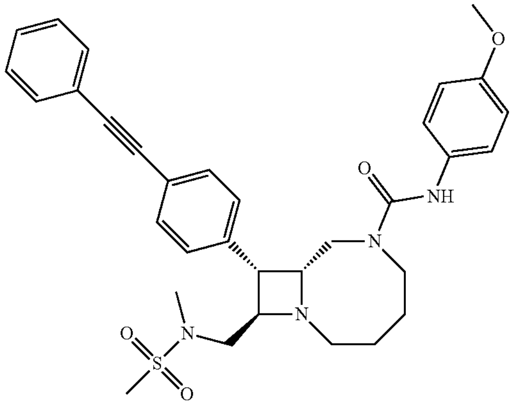 [SMILES: COc1ccc(NC(=O)N2CCCCN3[C@@H](C2)[C@@H](c2ccc(C#Cc4ccccc4)cc2)[C@@H]3CN(C)S(C)(=O)=O)cc1] | (8R,9R,10R)-N-(4-methoxyphenyl)-10-((N-methylmethylsulfonamido)methyl)-9-(4-(phenylethynyl)phenyl)-1,6-diazabicyclo[6.2.0]decane-6-carboxamide |
| 7 | 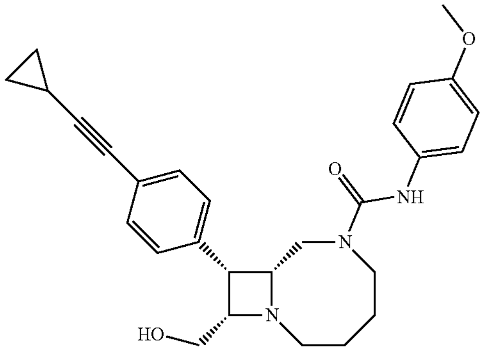 [SMILES: COc1ccc(NC(=O)N2CCCCN3[C@H](CO)[C@H](c4ccc(C#CC5CC5)cc4)[C@@H]3C2)cc1] | (8R,9R,10S)-9-(4-(cyclopropylethynyl)phenyl)-10-(hydroxymethyl)-N-(4-methoxyphenyl)-1,6-diazabicyclo[6.2.0]decane-6-carboxamide |
| 8 | 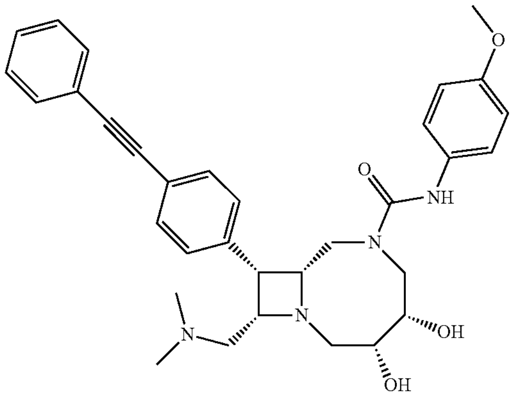 [SMILES: COc1ccc(NC(=O)N2C[C@H](O)[C@H](O)CN3[C@H](CN(C)C)[C@H](c4ccc(C#Cc5ccccc5)cc4)[C@@H]3C2)cc1] | (3R,4S,8R,9S,10S)-10-((dimethylamino)methyl)-3,4-dihydroxy-N-(4-methoxyphenyl)-9-(4-(phenylethynyl)phenyl)-1,6-diazabicyclo[6.2.0]decane-6-carboxamide |

TABLE 1-continued

| Comp. | Structure | Name |
| --- | --- | --- |
| 9 | 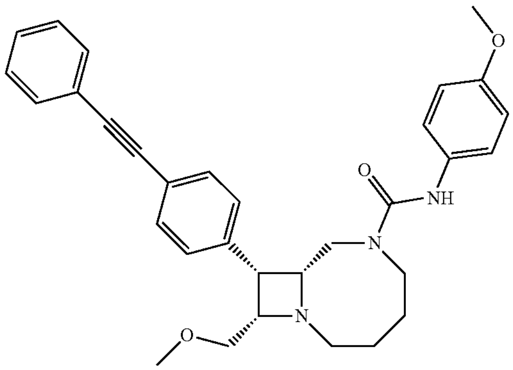 [SMILES: COC[C@@H]1[C@H](c2ccc(C#Cc3ccccc3)cc2)[C@@H]2CN(C(=O)Nc3ccc(OC)cc3)CCCCN12] | (8R,9R,10S)-10-(methoxymethyl)-N-(4-methoxyphenyl)-9-(4-(phenylethynyl)phenyl)-1,6-diazabicyclo[6.2.0]decane-6-carboxamide |
| 10 | 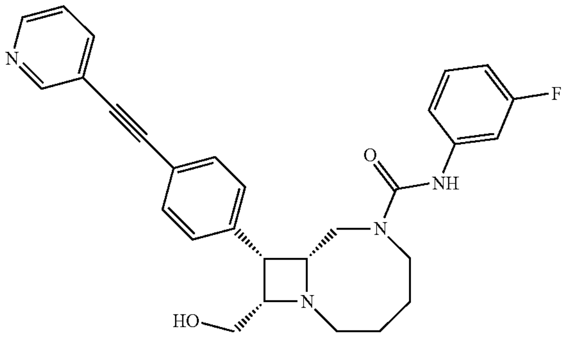 [SMILES: O=C(Nc1cccc(F)c1)N1CCCCN2[C@H](CO)[C@H](c3ccc(C#Cc4cccnc4)cc3)[C@@H]2C1] | (8R,9R,10S)-N-(3-fluorophenyl)-10-(hydroxymethyl)-9-(4-(pyridin-3-ylethynyl)phenyl)-1,6-diazabicyclo[6.2.0]decane-6-carboxamide |
| 11 | 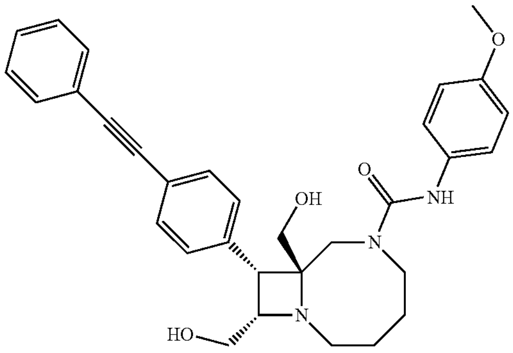 [SMILES: COc1ccc(NC(=O)N2CCCCN3[C@H](CO)[C@H](c4ccc(C#Cc5ccccc5)cc4)[C@]3(CO)C2)cc1] | (8R,9S,10S)-8,10-bis(hydroxymethyl)-N-(4-methoxyphenyl)-9-(4-(phenylethynyl)phenyl)-1,6-diazabicyclo[6.2.0]decane-6-carboxamide |
| 12 | 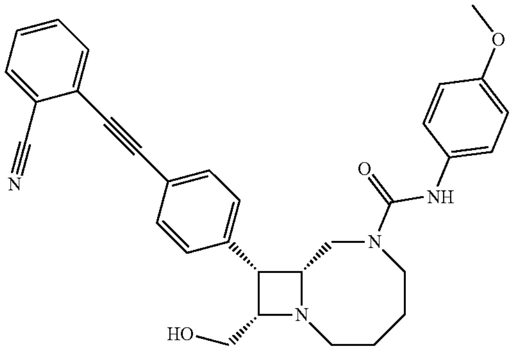 [SMILES: COc1ccc(NC(=O)N2CCCCN3[C@H](CO)[C@H](c4ccc(C#Cc5ccccc5C#N)cc4)[C@@H]3C2)cc1] | (8R,9R,10S)-9-(4-((2-cyanophenyl)ethynyl)phenyl)-10-(hydroxymethyl)-N-(4-methoxyphenyl)-1,6-diazabicyclo[6.2.0]decane-6-carboxamide |

TABLE 1-continued

| Comp. | Structure | Name |
|---|---|---|
| 13 | 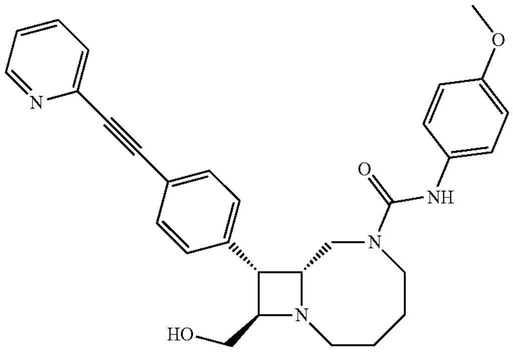 [SMILES: COc1ccc(NC(=O)N2CCCCN3[C@@H](CO)[C@H](c4ccc(C#Cc5ccccn5)cc4)[C@@H]3C2)cc1] | (8R,9R,10R)-10-(hydroxymethyl)-N-(4-methoxyphenyl)-9-(4-(pyridin-2-ylethynyl)phenyl)-1,6-diazabicyclo[6.2.0]decane-6-carboxamide |
| 14 | 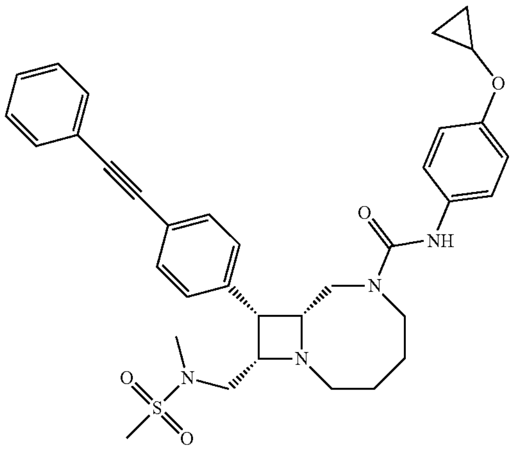 [SMILES: CN(C[C@@H]1[C@H](c2ccc(C#Cc3ccccc3)cc2)[C@@H]2CN(C(=O)Nc3ccc(OC4CC4)cc3)CCCCN12)S(C)(=O)=O] | (8R,9R,10S)-N-(4-cyclopropoxyphenyl)-10-((N-methylmethylsulfonamido)methyl)-9-(4-(phenylethynyl)phenyl)-1,6-diazabicyclo[6.2.0]decane-6-carboxamide |
| 15 | 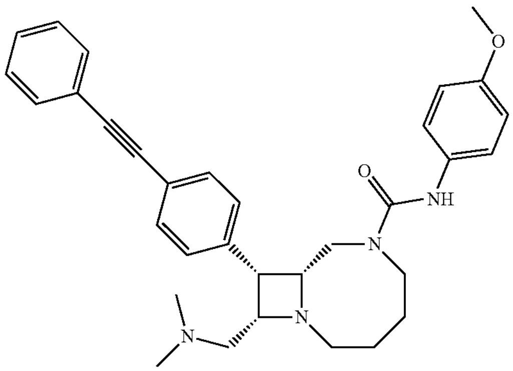 [SMILES: COc1ccc(NC(=O)N2CCCCN3[C@H](CN(C)C)[C@H](c4ccc(C#Cc5ccccc5)cc4)[C@@H]3C2)cc1] | (8R,9S,10S)-10-((dimethylamino)methyl)-N-(4-methoxyphenyl)-9-(4-(phenylethynyl)phenyl)-1,6-diazabicyclo[6.2.0]decane-6-carboxamide |
| 16 | 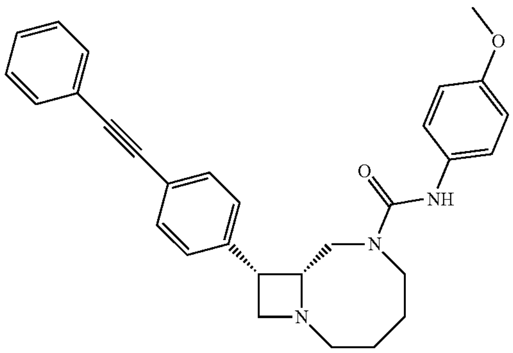 [SMILES: COc1ccc(NC(=O)N2CCCCN3C[C@H](c4ccc(C#Cc5ccccc5)cc4)[C@@H]3C2)cc1] | (8R,9S)-N-(4-methoxyphenyl)-9-4-(phenylethynyl)phenyl)-1,6-diazabicyclo[6.2.0]decane-6-carboxamide |

TABLE 1-continued

| Comp. | Structure | Name |
| --- | --- | --- |
| 17 | 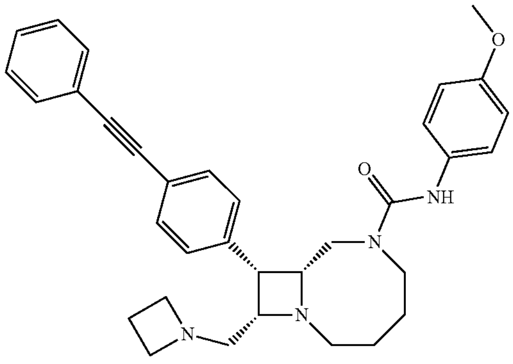 [SMILES: COc1ccc(NC(=O)N2CCCCN3[C@H](CN4CCC4)[C@H](c4ccc(C#Cc5ccccc5)cc4)[C@@H]3C2)cc1] | (8R,9S,10S)-10-(azetidin-1-ylmethyl)-N-(4-methoxyphenyl)-9-(4-(phenylethynyl)phenyl)-1,6-diazabicyclo[6.2.0]decane-6-carboxamide |
| 18 | 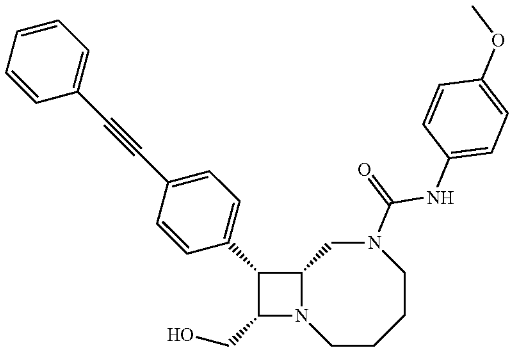 [SMILES: COc1ccc(NC(=O)N2CCCCN3[C@H](CO)[C@H](c4ccc(C#Cc5ccccc5)cc4)[C@@H]3C2)cc1] | (8R,9R,10S)-10-(hydroxymethyl)-N-(4-methoxyphenyl)-9-(4-(phenylethynyl)phenyl)-1,6-diazabicyclo[6.2.0]decane-6-carboxamide |
| 19 | 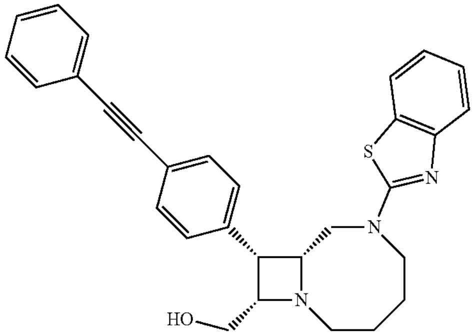 [SMILES: OC[C@@H]1[C@H](c2ccc(C#Cc3ccccc3)cc2)[C@@H]2CN(c3nc4ccccc4s3)CCCCN12] | ((8R,9R,10S)-6-(benzo[d]thiazol-2-yl)-9-(4-(phenylethynyl)phenyl)-1,6-diazabicyclo[6.2.0]decan-10-yl)methanol |
| 20 | 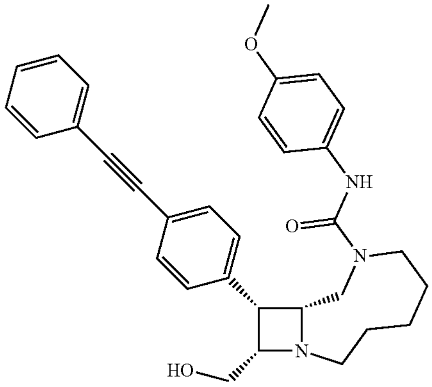 [SMILES: COc1ccc(NC(=O)N2CCCCCN3[C@H](CO)[C@H](c4ccc(C#Cc5ccccc5)cc4)[C@@H]3C2)cc1] | (9R,10R,11S)-11-(hydroxymethyl)-N-(4-methoxyphenyl)-10-(4-(phenylethynyl)phenyl)-1,7-diazabicyclo[7.2.0]undecane-7-carboxamide |

TABLE 1-continued

| Comp. | Structure | Name |
| --- | --- | --- |
| 21 | 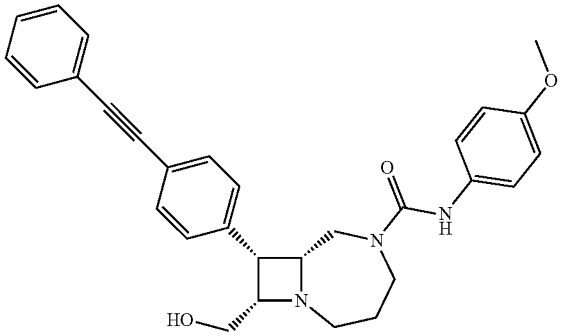 [SMILES: COc1ccc(NC(=O)N2CCCN3[C@H](CO)[C@H](c4ccc(C#Cc5ccccc5)cc4)[C@@H]3C2)cc1] | (7R,8R,9S)-9-(hydroxymethyl)-N-(4-methoxyphenyl)-8-(4-(phenylethynyl)phenyl)-1,5-diazabicyclo[5.2.0]nonane-5-carboxamide |

The compounds of the present disclosure include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethyl ammonium ion. Examples of prodrugs include $C_{1-6}$ alkyl esters of carboxylic acid groups, which, upon administration to a subject, are capable of providing active compounds.

Pharmaceutically acceptable salts of the compounds of the present disclosure include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the present disclosure and their pharmaceutically acceptable acid addition salts. Salts derived from appropriate bases include alkali metal (e.g., sodium), alkaline earth metal (e.g., magnesium), ammonium and N-$(alkyl)_4$ salts. The present disclosure also encompasses the quaternization of any basic nitrogen-containing groups of the compounds disclosed herein. Water or oil-soluble or dispersible products may be obtained by such quaternization. Salt forms of the compounds of any of the formulae herein can be amino acid salts of carboxyl groups (e.g., L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present disclosure provides compounds which are in a prodrug form. Prodrugs of the compounds described herein are those compounds that undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present disclosure which is administered as an ester (the "prodrug"), but then is metabolically hydrolyzed to the carboxylic acid, the active entity. Additional examples include peptidyl derivatives of a compound of the present disclosure.

The present disclosure also includes various hydrate and solvate forms of the compounds.

The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are intended to be encompassed within the scope of the present disclosure.

Methods

The compounds described herein are useful in the methods provided herein and, while not bound by any particular theory, are believed to exert their desirable effects through their ability to inhibit the growth of or kill *T. gondii* tachyzoites which are responsible for acute infections. Such compounds may also inhibit the growth of *T. gondii* bradyzoites, which are responsible for chronic infection. In some embodiments, the compounds may also inhibit the growth of *T. gondii* sporozoites which are responsible for infection following ingestion of oocysts. In some embodiments, the treatment includes causative prophylaxis, such as preventing the spread of *T. gondii*. In some embodiments, the treatment of infections caused by *T. gondii* refers to treatment intended to achieve cure, e.g., treatment for radical cure (i.e., clearing tachyzoites and/or bradyzoites from the subject).

In other embodiments, the compounds described herein may be useful in the treatment or prophylaxis of infections caused by parasites closely related to *Toxoplasma gondii*. In some embodiments, the parasites closely related to *Toxoplasma gondii* are *Sarcocystis neurona* and *Neospora caninum*. In certain embodiments, the compounds may be useful in the treatment or prophylaxis of protozoal myeloencephalitis. In some embodiments, the compositions may be useful in the treatment or prophylaxis of neosporosis.

Pharmaceutical Compositions

1. Formulations

For use in the methods described herein, the compounds can be formulated as pharmaceutical or veterinary compositions. The formulation selected can vary depending on the subject to be treated, the mode of administration, and the type of treatment desired (e.g., prevention, prophylaxis, or therapy). A summary of formulation techniques is found in *Remington: The Science and Practice of Pharmacy*, $21^{st}$ *Edition*, Lippincott Williams & Wilkins, (2005); and Encyclopedia of Pharmaceutical Technology, eds. J. Swarbrick and J. C. Boylan, 1988-1999, Marcel Dekker, New York, each of which is incorporated herein by reference. Exemplary routes of administration and formulations are described as follows.

In the practice of the disclosed methods, the compounds (or pharmaceutically acceptable salts thereof) or compositions can be administered by any of the usual and acceptable routes and methods known in the art. The compounds or compositions can thus be administered, for example, by the enteral or gastrointestinal route (e.g., orally or rectally), topically (e.g., to the skin or an accessible mucous membrane (e.g., an intraoral (e.g., sublingual or buccal), intranasal, intrarectal, or genitourinary surface)), parenterally (e.g., by intramuscular, intravenous, subcutaneous, intraarticular, intravesicular, intrathecal, epidural, ocular, or aural application or injection), transdermally, or by inhalation (e.g., by aerosol).

The compositions can be in the form of a solid, liquid, or gas, as determined to be appropriate by those of skill in the art. Thus, as general examples, the pharmaceutical compositions may be in the form of tablets, capsules, syrups, pills, enterically coated or other protected formulations, sustained release formulations, elixirs, powders, granulates, suspensions, emulsions, solutions, gels (e.g., hydrogels), pastes, ointments, creams, plasters, transdermal patches, drenches, suppositories, enemas, injectables, implants, sprays, or aerosols.

The compositions, in general, include an effective amount of a compound described herein and one or more pharmaceutically acceptable carriers or excipients, as is well known in the art. The compositions can thus include one or more diluents, buffers, preservatives, salts, carbohydrates, amino acids, carrier proteins, fatty acids, lipids, etc. The compounds described herein may be present in amounts totaling, for example, 0.1-95% by weight of the total weight of the composition (e.g., 0.1-1% by weight of the composition, 1-10% by weight of the composition, 10-20% by weight of the composition, 20-30% by weight of the composition, 30-40% by weight of the composition, etc.).

For injection, formulations can be prepared in conventional forms as liquid solutions or suspensions, or as solid forms suitable for solution or suspension in liquid prior to injection, or as emulsions. Suitable excipients for these formulations include, for example, water, saline, dextrose, and glycerol. Such compositions can also contain nontoxic auxiliary substances, such as wetting or emulsifying agents, and pH buffering agents, such as sodium acetate, sorbitan monolaurate, and so forth.

Formulations for oral use include tablets containing a compound in a mixture with one or more non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, and buffering agents.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The pharmaceutical composition may also be formulated as a veterinary composition, intended for use with subjects other than humans. The veterinary compositions according to the present disclosure can be in any appropriate forms to suit the requested administration modes, for instance nasal, oral, intradermic, cutaneous or parenteral. In certain embodiments, the composition is in a form intended for an oral administration and, for instance when the domestic animal eating, either mixed to the food ration, or directly into the mouth after meal. The veterinary compositions of the disclosure are in the form of a nasal, oral or injectable liquid suspension or solution, or in solid or semi-solid form, powders, pellets, capsules, granules, sugar-coated pills, gelules, sprays, cachets, pills, tablets, pastes, implants or gels. In a particular embodiment, the compositions are in the form of an oral solid form such as tablets. In some embodiments, the veterinary compositions may have an effective amount of the compound for a specific species of animal (e.g., cow, lamb, goat, horse, dog, poultry such as chicken, or turkey, etc.). In certain embodiments, the veterinary composition is formulated for the treatment or prophylaxis of *Toxoplasma gondii, Sarcocystis neurona*, and/or *Neospora caninum*. The veterinary composition may be formulated for the treatment or prophylaxis of protozoal myeloencephalitis in horses. In some embodiments, the veterinary composition may be formulated for the treatment or prophylaxis of neosporosis in cattle and dogs.

In specific embodiments, the compositions of the disclosure are formulated in pellets or tablets for an oral administration. According to this type of formulation, they comprise lactose monohydrate, cellulose microcrystalline, crospovidone/povidone, aroma, compressible sugar and magnesium stearate as excipients. When the compositions are in the form of pellets or tablets, they are for instance 1 mg, 2 mg, or 4 mg torasemide pellets or tablets. Such pellets or tablets are divisible so that they can be cut to suit the posology according to the disclosure in one or two daily takes. In certain embodiments, the compositions may be formulated in injectable solutions or suspensions for a parenteral administration. The injectable compositions are produced by mixing therapeutically efficient quantity of torasemide with a pH regulator, a buffer agent, a suspension agent, a solubilization agent, a stabilizer, a tonicity agent and/or a preservative, and by transformation of the mixture into an intravenous, sub-cutaneous, intramuscular injection or perfusion according to a conventional method. Possibly, the injectable compositions may be lyophilized according to a conventional method. Examples of suspension agents include methylcellulose, polysorbate 80, hydroxyethylcellulose, xanthan gum, sodic carboxymethylcellulose and polyethoxylated sorbitan monolaurate. Examples of solubilisation agent include polyoxy ethylene-solidified castor oil, polysorbate 80, nicotinamide, polyethoxylated sorbitan monolaurate, macrogol and ethyl ester of caste oil fatty acid. Moreover, the stabilizer includes sodium sulfite, sodium metalsulfite and ether, while the preservative includes methyl p-hydroxybenzoate, ethyl p-hydroxybenzoate, sorbic acid, phenol, cresol and chlorocresol. An example of tonicity agent is mannitol. When preparing injectable suspensions or solutions, it is desirable to make sure that they are blood isotonic.

2. Dosage

The dose of a compound depends on a number of factors, such as the manner of administration, the age and the body weight of the subject, and the condition of the subject to be treated, and ultimately will be decided by the attending physician or veterinarian. Such an amount of the compound, as determined by the attending physician or veterinarian, is referred to herein, and in the claims, as a “therapeutically effective amount.” For example, the dose of a compound disclosed herein is typically in the range of about 1 to about 1000 mg per day. The therapeutically effective amount may be, for example, an amount of from about 1 mg to about 500 mg per day.

Administration of each drug, as described herein, can, independently, be one to four times daily for one day to one year, and may even be for the life of the subject. Chronic, long-term administration may be indicated.

3. Kits

The compounds and compositions can be packaged in a kit, optionally with one or more other pharmaceutical agents (see below). Non-limiting examples of the kits include those that contain, e.g., two or more pills, a pill and a powder, a suppository and a liquid in a vial, or two topical creams. The kits can include optional components that aid in the administration of the unit dose to subjects, such as vials for reconstituting powder forms, syringes for injection, customized IV delivery systems, or inhalers. Additionally, the unit dose kits can contain instructions for preparation and administration of the compositions. The kits can be manufactured as a single use unit dose for one subject, multiple uses for a particular subject (at a constant dose or in which the individual compounds may vary in potency as therapy progresses); or the kits can contain multiple doses suitable for administration to multiple subjects (“bulk packaging”). The kit components can be assembled in cartons, blister packs, bottles, and tubes.

4. Combination Therapies

The compounds and pharmaceutical compositions can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder, or they may achieve different effects (e.g., control of any adverse effects). In some embodiments, the combination therapy may comprise administration of one or more of Compounds having the structure of formula (I), (II), (III), and/or (IV) with another antibiotic for the treatment of *T. gondii* infection. For example, the antibiotic may be selected from pyrimethamine, sulfadiazine, clindamycin, and mirincamycin. In some embodiments the combination therapy may comprise administration of one or more of Compounds 1-21.

EXAMPLES

The following examples illustrate specific aspects of the instant description. The examples should not be construed as limiting, as the example merely provides specific understanding and practice of the embodiments and its various aspects.

Compounds were synthesized by conventional methods known in the art. At the time of pulling the compounds out of storage for retesting at dose, the compounds were put through a quality control step to ensure all compounds were of the correct mass and greater than 85% pure.

Example 1: $EC_{50}$ Measurements on *T. gondii*

*Toxoplasma gondii* tachyzoites (ME49-FLUC, type 2) (27) were serially passaged in human foreskin fibroblasts (HFF) cultured in complete DMEM medium (DMEM supplemented with 10% fetal bovine serum (FBS), glutamine (10 mM) and gentamycin (10 μg/mL)). For each assay described, infected monolayers were scraped, needle passed (23 ga), and parasites were separated from host cell debris using a three (3) micron pore polycarbonate filter. HeLa cells were cultured in MEM media that contained 10% FBS, 4 mM L-glutamine and 10 mM HEPES solution. Cell culture and assays were conducted using a 37° C. incubator with 5% $CO_2$. Cell cultures were negative for *mycoplasma*, as determined using the e-Myco plus kit (Intron Biotechnology).

White, clear bottom 96-well assay plates were set up as described above with the following modifications. Only the inner 60 wells were used for the assay in order to reduce variability that results from evaporation during incubation. Dilution of compound stock is as described above, with all wells containing a final concentration of 0.1% DMSO. DMSO (vehicle control) and pyrimethamine (2.5 μM, positive control) were included in the outside wells of all plates as controls. Liquid handling (serial dilutions, compound dilutions, cell feeding, plate-to-plate transfers, etc.) utilized a Dual Pod Biomek FX. Luciferase assays were performed using the integrated and automated platform (Beckman Coulter). The SAMI EX software was used to design and execute the screening assay and enabled efficient and uniform assay execution across all the assay plates. Table 2 shows the $EC_{50}$ values measured for *Toxoplasma gondii* for several compounds having the structure of formula (I).

TABLE 2

| Comp. | Structure (SMILES string)† | $EC_{50}$ (μM) |
|---|---|---|
| 1 | 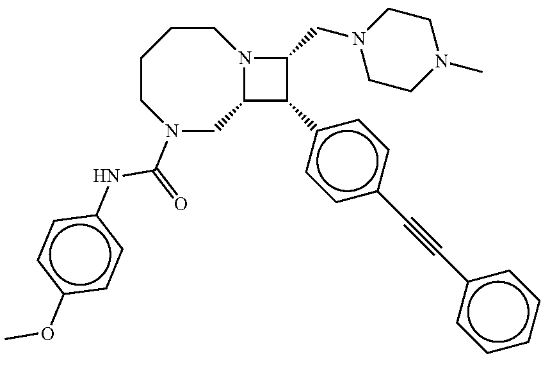<br>(COc1ccc(NC(=O)N2CCCCN3[C@H](CN4CCN(C)CC4)[C@@H]([C@@H]3 C2)c2ccc(cc2)C#Cc2ccccc2)cc1) | 0.4249 |
| 2 | 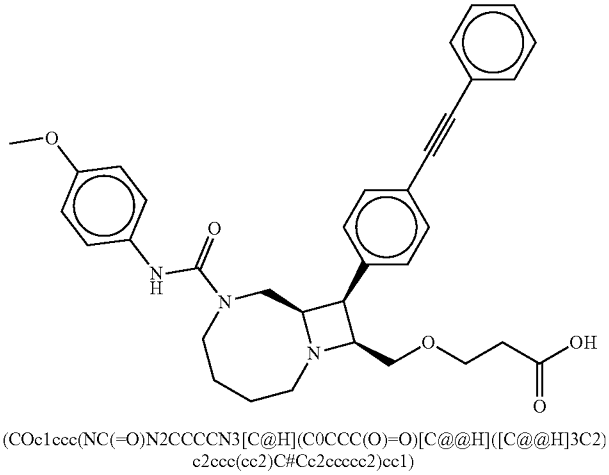<br>(COc1ccc(NC(=O)N2CCCCN3[C@H](COCCC(O)=O)[C@@H]([C@@H]3C2) c2ccc(cc2)C#Cc2ccccc2)cc1) | 0.06428 |

TABLE 2-continued
| Comp. | Structure (SMILES string)† | $EC_{50}$ (μM) |
|---|---|---|
| 3 | 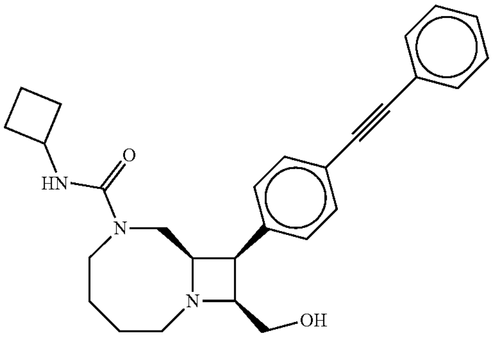 (OC[C@@H]1[C@@H]([C@@H]2CN(CCCCN12)C(=O)NC1CCC1)c1ccc(cc1)C#Cc1ccccc1) | 2.575 |
| 4 | 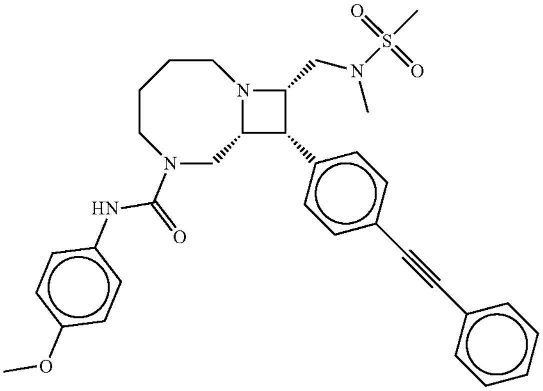 (COc1ccc(NC(=O)N2CCCCN3[C@H](CN(C)S(C)(=O)=O)[C@@H]([C@@H]3C2)c2ccc(cc2)C#Cc2ccccc2)cc1) | 0.03476 |
| 5 | 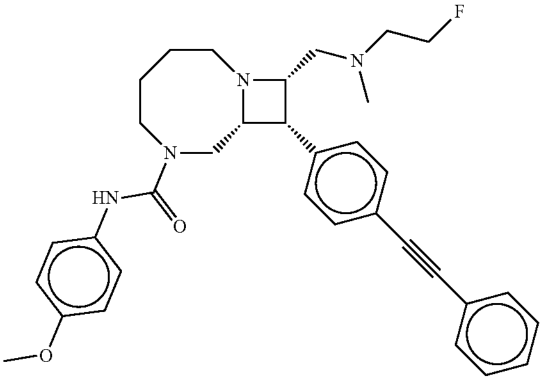 (COc1ccc(NC(=O)N2CCCCN3[C@H](CN(C)CCF)[C@@H]([C@@H]3C2)c2ccc(cc2)C#Cc2ccccc2)cc1) | 0.08952 |

TABLE 2-continued
| Comp. | Structure (SMILES string)† | $EC_{50}$ (μM) |
|---|---|---|
| 6 | 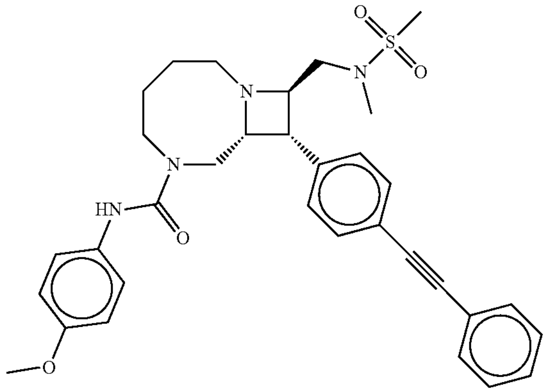 (COc1ccc(NC(=O)N2CCCCN3[C@@H](CN(C)S(C)(=O)=O)[C@@H]([C@@H]3C2)c2ccc(cc2)C#Cc2ccccc2)cc1) | 0.03999 |
| 7 | 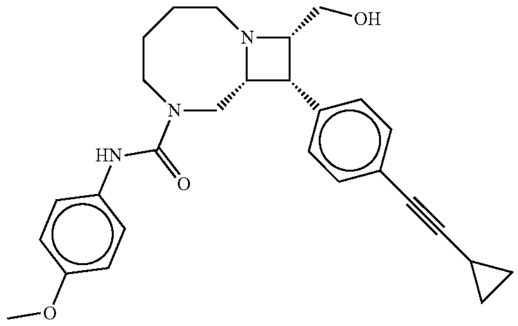 (COc1ccc(NC(=O)N2CCCCN3[C@H](CO)[C@@H]([C@@H]3C2)c2ccc(cc2)C#CC2CC2)cc1) | 1.609 |
| 8 | 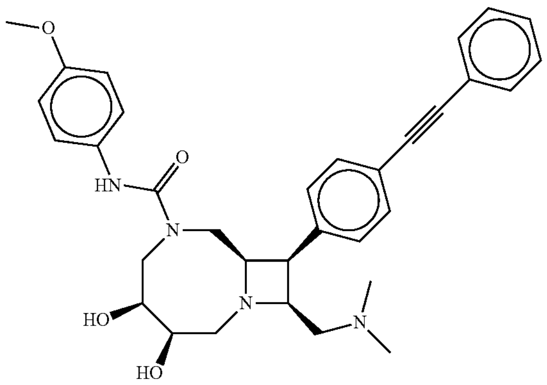 (COc1ccc(NC(=O)N2C[C@H]3[C@H]([C@@H](CN(C)C)N3C[C@@H](O)[C@@H](O)C2)c2ccc(cc2)C#Cc2ccccc2)cc1) | 0.03927 |

TABLE 2-continued
| Comp. | Structure (SMILES string)† | $EC_{50}$ (μM) |
|---|---|---|
| 9 | 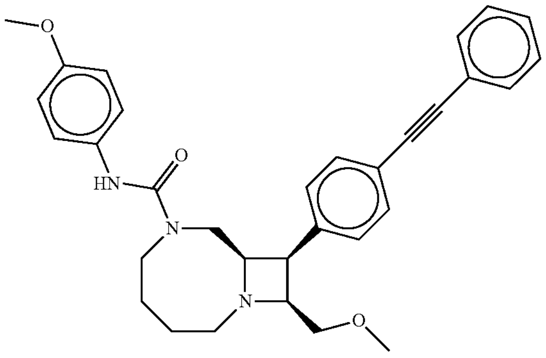<br>(COC[C@@H]1[C@@H]([C@@H]2CN(CCCCN12)C(=O)Nc1ccc(OC)cc1)c1ccc(cc1)C#Cc1ccccc1) | 0.05035 |
| 10 | 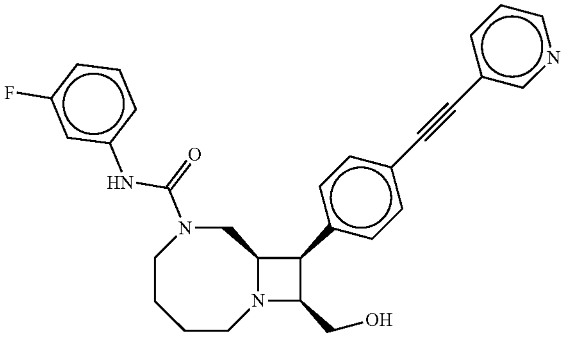<br>(OC[C@@H]1[C@@H]([C@@H]2CN(CCCCN12)C(=O)Nc1cccc(F)c1)c1ccc(cc1)C#Cc1cccnc1) | 0.4926 |
| 11 | 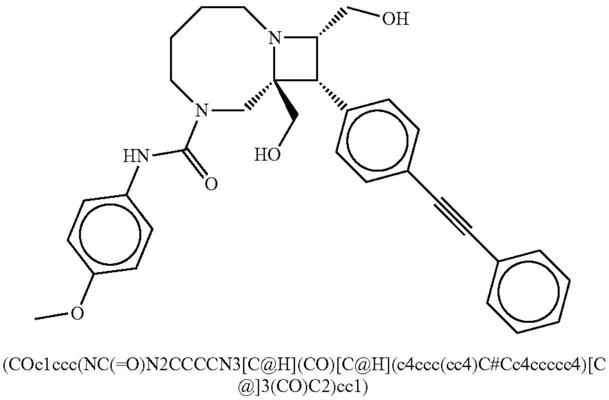<br>(COc1ccc(NC(=O)N2CCCCN3[C@H](CO)[C@H](c4ccc(cc4)C#Cc4ccccc4)[C@]3(CO)C2)cc1) | 1.687 |

TABLE 2-continued
| Comp. | Structure (SMILES string)† | $EC_{50}$ (μM) |
|---|---|---|
| 12 | 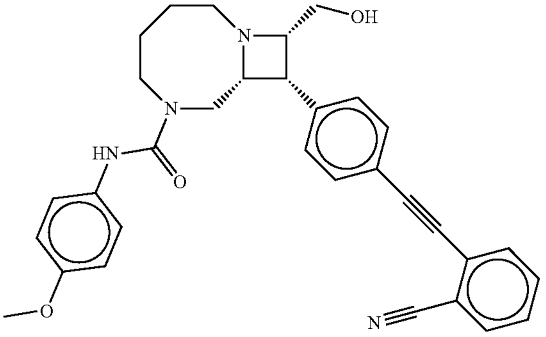 (COc1ccc(NC(=O)N2CCCCN3[C@H](CO)[C@@H]([C@@H]3C2)c2ccc(cc2) C#Cc2ccccc2C#N)cc1) | 0.2134 |
| 13 | 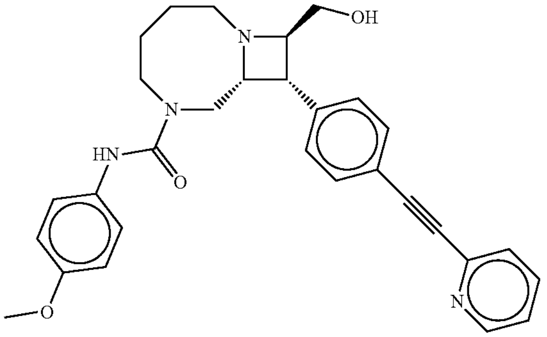 (COc1ccc(NC(=O)N2CCCCN3[C@@H](CO)[C@@H]([C@@H]3C2)c2ccc(cc 2)C#Cc2ccccn2)cc1) | 0.6463 |
| 14 | 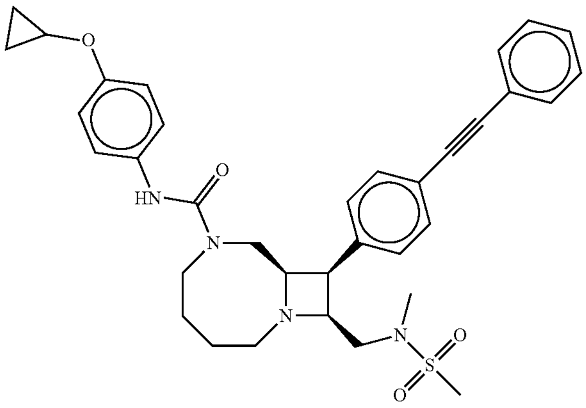 (CN(C[C@@H]1[C@@H]([C@@H]2CN(CCCCN12)C(=O)Nc1ccc(OC2CC2) cc1)c1ccc(cc1)C#Cc1ccccc1)S(C)(=O)=O) | 0.01849 |

TABLE 2-continued
| Comp. | Structure (SMILES string)† | $EC_{50}$ (μM) |
|---|---|---|
| 15 | 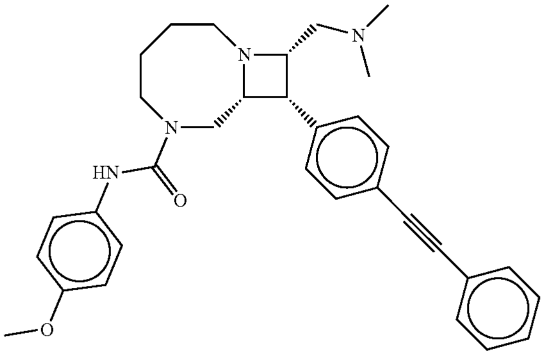<br>(COc1ccc(NC(=O)N2CCCCN3[C@H](CN(C)C)[C@@H]([C@@H]3C2)c2ccc(cc2)C#Cc2ccccc2)cc1) | 0.0226 |
| 16 | 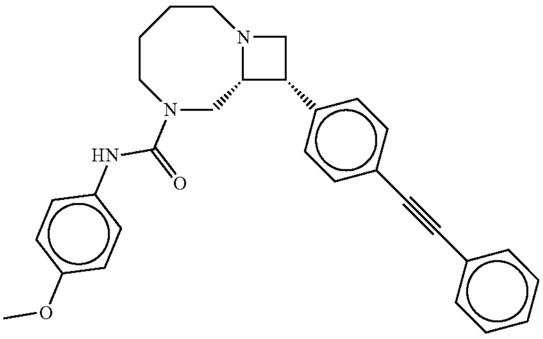<br>(COc1ccc(NC(=O)N2CCCCN3[C@@H]([C@@H]3C2)c2ccc(cc2)C#Cc2ccccc2)cc1) | 0.07697 |
| 17 | 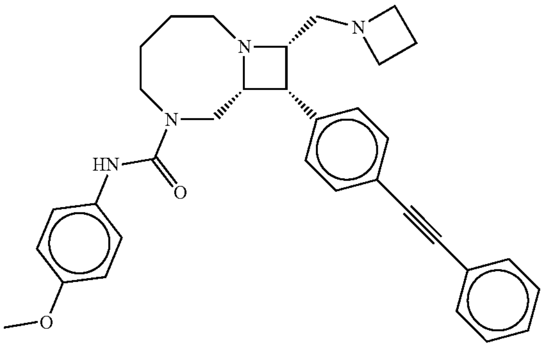<br>(COc1ccc(NC(=O)N2CCCCN3[C@H](CN4CCC4)[C@@H]([C@@H]3C2)c2ccc(cc2)C#Cc2ccccc2)cc1) | 0.4416 |

TABLE 2-continued
| Comp. | Structure (SMILES string)† | $EC_{50}$ (μM) |
|---|---|---|
| 18 | 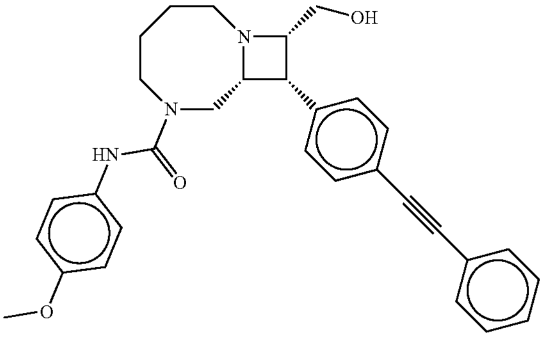<br>(COc1ccc(NC(=O)N2CCCCN3[C@H](CO)[C@@H]([C@@H]3C2)c2ccc(cc2)<br>C#Cc2ccccc2)cc1) | 0.02885 |
| 19 | 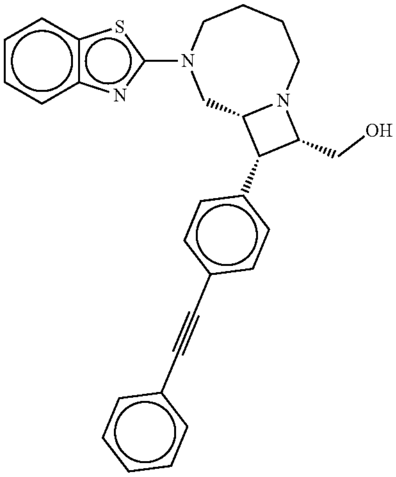<br>(OC[C@@H]1[C@@H]([C@@H]2CN(CCCCN12)c1nc2ccccc2s1)c1ccc(cc1)<br>C#Cc1ccccc1) | 3.944 |
| 20 | 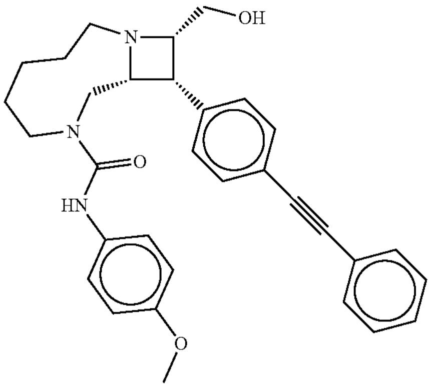<br>(COc1ccc(NC(=O)N2CCCCCN3[C@H](CO)[C@@H]([C@@H]3C2)c2ccc(cc<br>2)C#Cc2ccccc2)cc1) | 0.1693 |

TABLE 2-continued

| Comp. | Structure (SMILES string)† | $EC_{50}$ (μM) |
|---|---|---|
| 21 | 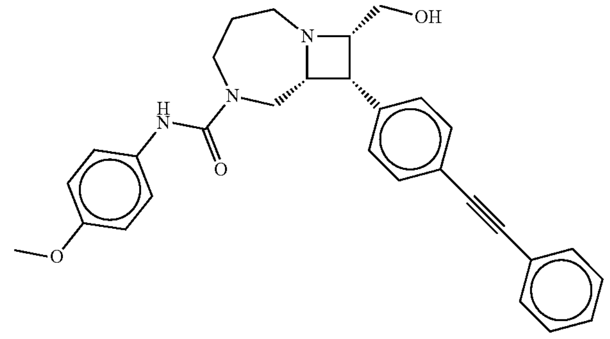 (COc1ccc(NC(=O)N2CCCN3[C@H](CO)[C@@H]([C@@H]3C2)c2ccc(cc2)C#Cc2ccccc2)cc1) | 1.748 |

†It will be understood that in the event of discrepancy between the illustrated structure and SMILES string in Table 2, both compounds with the illustrated structure and compounds with the SMILES string will be considered as embraced by the present disclosure.

Example 2: EC50 Measurements on *N. caninum*

*Neospora caninum* parasites (NC-1 strain) expressing a lac-Z transgene (1) were serially passaged as tachyzoites in human foreskin fibroblasts cultured in DMEM supplemented with 10% fetal bovine serum (FBS), glutamine (10 mM) and gentamycin (10 μg/mL). Mature cultures were scraped, syringe passed using a 25 g needle to release parasites, filtered through a 3 micron polycarbonate filter to remove host cell debris and counted prior to each assay. All cultures were maintained in a 37° C. incubator with 5% $CO_2$ and were verified *mycoplasma* free using the e-Myco plus *Mycoplasma* PCR detection kit (Boca Scientific).

Compounds were prepared as 10 mM stock in 100% DMSO. Pyrimethamine (positive control) and DMSO were included as controls in all plates and all replicates. The $EC_{50}$ values were determined using a 10-point dose response curve using a 2-fold dilution series from 5.0 μM to 0.01 μM across the plate. Experiments were conducted in 96-well plates containing confluent HFF cells. Each assay plate was inoculated with $1\times10^3$ parasites (100 μL) containing 100 μL of 2× compound and incubated for 72 h prior to preparation for the j-Gal assay as described in Seeber, F. et al., Gene 169 (1996): 39-45, hereby incorporated by reference in its entirety and particularly in relation to the β-Gal assay protocol. Briefly, culture medium was replaced, wells rinsed with 200 μL of PBS followed by incubation with 50 μL of lysis buffer (100 mM HEPES, 1 mM $MgSO_4$, 1% Triton X-100, 5 mM DTT) for 10 min at 50° C. Following lysis step, 160 μL of assay buffer (100 mM phosphate buffer (82 mM $Na_2HPO_4$ (dibasic, anhydrous), 31 mM $Na_2HPO_4$ (monobasic, dihydrate), 102 mM β-ME, 9 mM $MgCl_2$) was added to each well (210 μL total volume) and incubated for 10 mins at 37° C. Next, 40 μL of 1×CPRG substrate (chlorophenol red-b-D-galactopyranoside: 10× stock CPRG: 62.5 mM CPRG diluted in phosphate buffer as described above) was added to each well (250 μL total volume) and incubated at 37° C. for 5 mins prior to evaluation of β-Gal expression on BioTek EL×800 plate reader (A570 nm). All wells contained from 0.1-0.05% DMSO.

Table 3 shows the activities of several bicyclic azetidine compounds of the present disclosure against *N. caninum* as indicated by the $EC_{50}$ value. $EC_{50}$ values determined from 10-point dose response curve (5 μM-0.01 μM) and presented as the average of three biological replicates. Linear regression and dose response inhibition (log ([compound]) vs normalized response-variable slope) were performed with Prism 8 for Mac (Graphpad Software, Inc.) and both the fits and data are shown in FIG. 1. Values represent the average of three biological replicates each with two internal replicates and are plotted as mean±S.E.M.

TABLE 3

| Compound | $EC_{50}$ (μM) |
|---|---|
| 15 | 0.250 |
| 8 | 0.030 |
| 14 | 0.037 |
| 16 | 0.193 |
| 20 | 0.157 |
| 6 | 0.060 |
| Pyrimethamine (Pyr) | 0.263 |

Example 3: $EC_{50}$ Measurements of Compound 15 Across Different *T. gondii* Strains The ability of bicyclic azetidines to inhibit different strains of *T. gondii* was tested using a series of firefly luciferase (FLUC)-tagged lines. The following FLUC-expressing strains were recently described: ME49 (type 2), CTG (type 3), RUB (type 5), VAND (Type 10) in Hopper A T *J Med Chem* 62 (2019): 1562-1576 hereby incorporated by reference in its entirety and particularly in relation to the FLUC-expressing strains of *T. gondii*. A similar strategy was utilized to derive FLUC expressing lines from additional *T. gondii* strains MAS (type 4) and FOU (type 6). *Toxoplasma gondii* strains expressing FLUC were grown in vitro as tachyzoites and used for 10 point dose-response inhibition assays using protocols described above in Examples 1 and 2. Sensitivity to growth inhibition of each strain by Compound 15 concentrations was measured, in comparisons to the reference strain ME49 FLUC. All of the strains showed very close $EC_{50}$ values falling within 2-fold of each other and historical standards (Table 4). In Table 4, $EC_{50}$ values are reported in nM derived from three or more independent titrations.

These findings suggest that the compounds described herein provide potent inhibition across multiple genotypes of *T. gondii*, including those that represent diverse clinical outcomes in humans.

TABLE 4

| | *Toxoplasma gondii* strains | | | | | |
|---|---|---|---|---|---|---|
| Genotype | ME49 2 | CTG 3 | MAS 4 | RUB 5 | FOU 6 | VAND 10 |
| Average $EC_{50}$ ± S.D. | 49.4 ± 9.3 | 34.3 ± 7.9 | 41.9 ± 15.6 | 26.9 ± 9.6 | 45.1 ± 12.2 | 27.9 ± 6.7 |

Other Embodiments

The disclosures of each and every patent, patent application, and publication cited herein are hereby incorporated herein by reference in their entirety. Also incorporated by reference is the disclosure of US Publication No. US 2016/0289235 A1 and Int'l Publication No WO 2018175385 A1. In particular embodiments, a compound of the disclosure is not a compound described in Table 1 of US Publication No. US 2016/0289235 A1 and/or a compound described in Table 1 of Int'l Publication No WO 2018175385 A1.

As various changes can be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings. Accordingly, the present description is intended to embrace all such alternatives, modifications and variances which fall within the scope of the appended claims.

The invention claimed is:

1. A method of treatment or prophylaxis of *Toxoplasma gondii* infection, *Sarcocystis neurona* infection, or *Neospora caninum* infection in a subject in need thereof comprising administering to said subject a compound having the structure of formula (I):

(I)

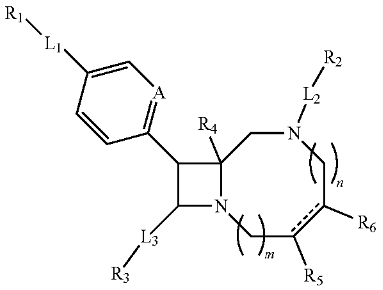

wherein the dashed bond (- - -) may be a single or double bond;

m is 0 (i.e., it is a bond) or 1;

n is 0, 1 or 2;

A is CH or N;

$L_1$ is absent (i.e., it is a bond), or —C≡C—;

$L_2$ is absent, alkylene, —C(O)NR—; —$SO_2$—, or —C(O)—;

$L_3$ is absent, alkylene, or heteroalkylene;

$R_1$ is hydrogen, heteroalkyl, aryl, heteroaryl, or cycloalkyl, and $R_1$ is optionally substituted;

$R_2$ is perfluoroalkyl, aryl, arylalkyl, alkyl, heteroaryl, or cycloalkyl, and $R_2$ is optionally substituted;

$R_3$ is —N(R)S(O)$_2$R;

$R_4$ is hydrogen or —$CH_2OH$;

$R_5$ and $R_6$ are independently selected from hydrogen and OH; and

R is independently selected at each occurrence from hydrogen and lower alkyl, wherein R is optionally substituted.

2. The method according to claim 1, wherein said compound has the structure of formula (II):

(II)

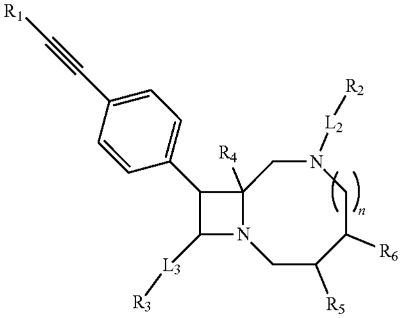

wherein n is 0 (i.e. it is a bond) or 1;

$L_2$ is absent or —C(O)NH—;

$L_3$ is absent or —$CH_2$—

$R_1$ is aryl, heteroaryl, or cycloalkyl group, and $R_1$ is optionally substituted with —CN;

$R_2$ is aryl, heteroaryl, or cycloalkyl, and $R_2$ is optionally substituted with halogen or —OR;

$R_3$ is —N(R)S(O)$_2$R;

$R_4$ is hydrogen or —$CH_2OH$;

$R_5$ and $R_6$ are independently selected from hydrogen and OH; and

R is independently selected at each occurrence from alkyl or cycloalkyl and R is optionally substituted with halogen, —OH, or —COOH.

3. The method according to claim 1, wherein said compound has the structure of formula (IIa):

(IIa)

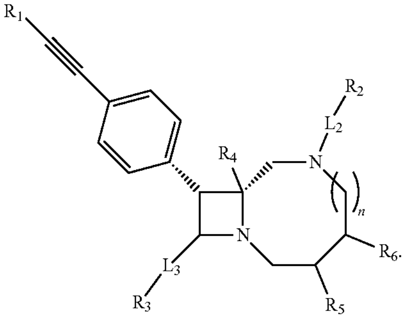

4. The method according to claim 1, wherein $L_2$ is —C(O)NH— and $R_2$ is phenyl optionally substituted with halogen or —OR.

5. The method according to claim 1, wherein said compound has the structure of formula (III):

(III)

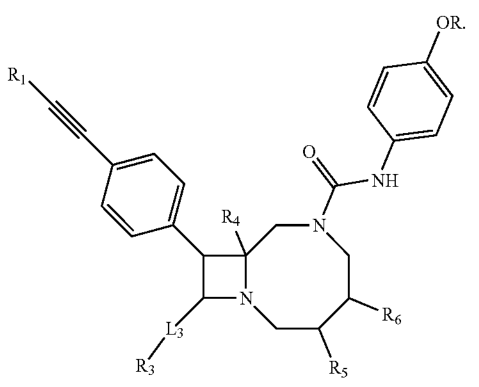

6. The method according to claim 1, wherein said compound has the structure of formula (IV):

(IV)

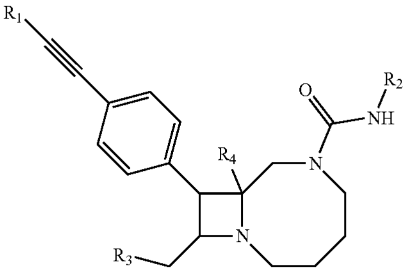

wherein $R_1$ is aryl, heteroaryl, or cycloalkyl, and $R_1$ is optionally substituted with —CN;

$R_2$ is aryl, heteroaryl, or cycloalkyl, and $R_2$ is optionally substituted with halogen or —OR;

$R_3$ is —N(R)S(O)$_2$R;

$R_4$ is hydrogen or —$CH_2OH$; and

R is independently selected at each occurrence from alkyl or cycloalkyl, and R is optionally substituted with halogen, —OH, or —COOH.

7. The method according to claim 1, wherein said compound has the structure:

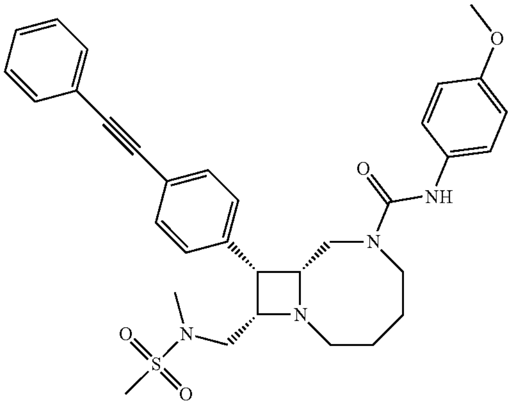

,

-continued

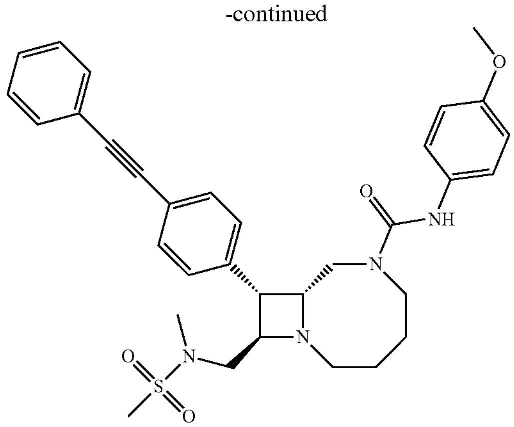

, or

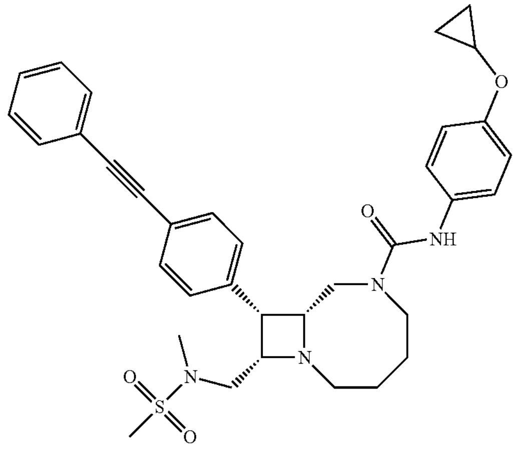

.

8. The method according to claim 1, wherein said subject is human.

9. The method according to claim 1, wherein said subject is a mouse, rat, cat, dog, chicken, turkey, rabbit, non-human primate, lizard, gecko, cow, calf, sheep, goat, lamb, horse, foal, pig, or piglet.

10. The method according to claim 1, wherein said compound is co-administered with one or more antibiotics selected from pyrimethamine, sulfadiazine, and clindamycin.

11. The method according to claim 1, wherein said infection is caused from *Toxoplasma gondii*.

12. A compound having the structure of formula (IV):

(IV)

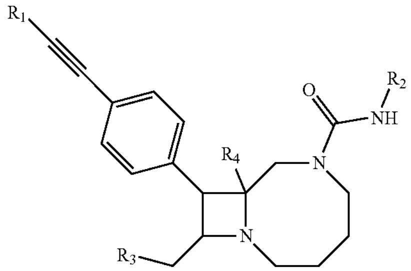

wherein $R_1$ is aryl, heteroaryl, or cycloalkyl optionally substituted with —CN;

$R_2$ is aryl, heteroaryl, or cycloalkyl optionally substituted with halogen or —OR;

$R_3$ is —N(R)S(O)$_2$R;

$R_4$ is hydrogen or —$CH_2OH$; and

R is independently selected at each occurrence from alkyl or cycloalkyl optionally substituted with halogen, or —OH.

13. The compound according to claim 12, wherein said compound has the structure:

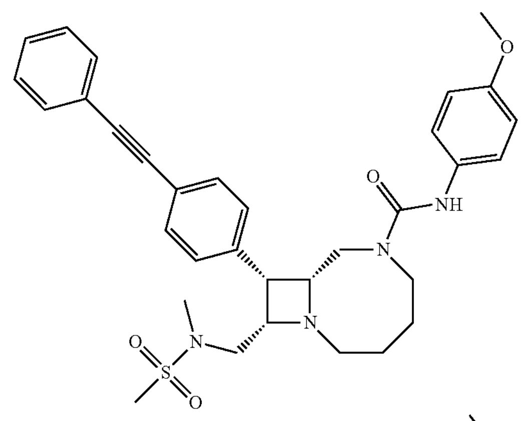

,

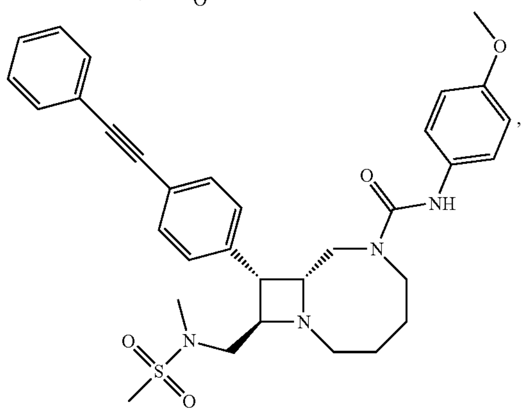

, or

-continued

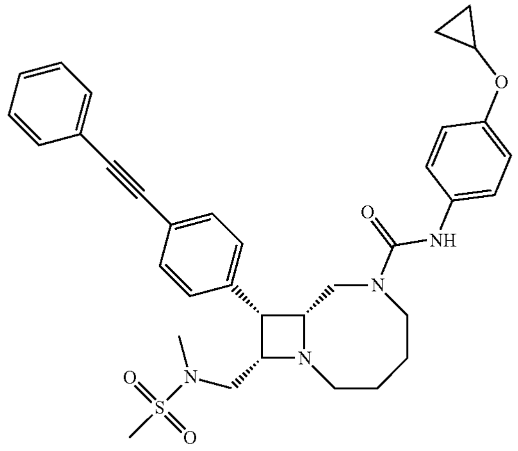

.

14. A pharmaceutical composition comprising a pharmaceutically acceptable excipient and the compound according to claim 12, or a pharmaceutically acceptable salt or prodrug thereof.

15. The pharmaceutical composition according to claim 14, formulated as a veterinary composition.

16. The pharmaceutical composition according to claim 14, wherein said compound is present in an effective amount to inhibit infection of *Toxoplasma gondii, Sarcocystis neurona*, or *Neospora caninum* in a subject.

17. The pharmaceutical composition according to claim 16, wherein said subject is human.

18. The pharmaceutical composition according to claim 14, wherein said composition further comprises one or more antibiotics selected from pyrimethamine, sulfadiazine, clindamycin, and mirincamycin.

* * * * *